United States Patent
Long et al.

(10) Patent No.: US 10,226,386 B2
(45) Date of Patent: Mar. 12, 2019

(54) METHODS AND APPARATUSES FOR SEPARATING DISCRETE ARTICLES FROM CONTINUOUS WEBS

(71) Applicant: The Procter & Gamble Company, Cincinnati, OH (US)

(72) Inventors: Michael Devin Long, Springfield Township, OH (US); Todd M. Fegelman, Wyoming, OH (US); Chad Burnett, Cincinnati, OH (US); Jeffry Rosiak, Loveland, OH (US); Paul Gerald Tiettmeyer, Harrison, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/716,548

(22) Filed: Sep. 27, 2017

(65) Prior Publication Data

US 2018/0092783 A1 Apr. 5, 2018

Related U.S. Application Data

(60) Provisional application No. 62/402,129, filed on Sep. 30, 2016.

(51) Int. Cl.
| | |
|---|---|
| *B26D 7/26* | (2006.01) |
| *A61F 13/15* | (2006.01) |
| *B26D 1/40* | (2006.01) |
| *B26D 11/00* | (2006.01) |
| *A61F 13/49* | (2006.01) |
| *B26D 1/62* | (2006.01) |
| *B65H 35/00* | (2006.01) |
| *B65H 35/08* | (2006.01) |

(52) U.S. Cl.
CPC ........ *A61F 13/15723* (2013.01); *B26D 1/405* (2013.01); *B26D 7/26* (2013.01); *B26D 11/00* (2013.01); *A61F 13/15764* (2013.01); *A61F 13/49011* (2013.01); *B26D 1/62* (2013.01); *B65H 35/008* (2013.01); *B65H 35/08* (2013.01)

(58) Field of Classification Search
CPC .......... B26D 7/26; B26D 1/405; B65H 35/08; B65H 35/008
See application file for complete search history.

(56) References Cited

U.S. PATENT DOCUMENTS

| | | | |
|---|---|---|---|
| 4,940,464 A | 7/1990 | Van Gompel et al. | |
| 5,092,861 A | 3/1992 | Nomura et al. | |
| 5,246,433 A | 9/1993 | Hasse et al. | |
| 5,407,507 A * | 4/1995 | Ball | A61F 13/15601 |
| | | | 156/163 |
| 5,569,234 A | 10/1996 | Buell et al. | |
| 5,897,545 A | 4/1999 | Kline et al. | |

(Continued)

FOREIGN PATENT DOCUMENTS

DE 102006016410 11/2007

OTHER PUBLICATIONS

International Search Report and Written Opinion, PCT/US2017/053574, dated Nov. 24, 2017.

*Primary Examiner* — Sean M Michalski
(74) *Attorney, Agent, or Firm* — Christian M. Best

(57) ABSTRACT

Methods of separating discrete articles from continuous webs are disclosed. The methods use a separation assembly. The present disclosure further includes a cutting assembly and a pair of cutting rolls for use in the separation assembly.

20 Claims, 18 Drawing Sheets

(56) References Cited

U.S. PATENT DOCUMENTS

| | | | |
|---|---|---|---|
| 5,957,908 A | 9/1999 | Kline et al. | |
| 6,120,487 A | 9/2000 | Ashton | |
| 6,120,489 A | 9/2000 | Johnson et al. | |
| 9,327,417 B2 * | 5/2016 | Saga | B26D 1/405 |
| 2003/0233082 A1 | 12/2003 | Kline et al. | |
| 2009/0266209 A1 * | 10/2009 | Thielges | B21D 28/346 |
| | | | 83/140 |
| 2012/0167736 A1 * | 7/2012 | Yokoe | B26D 1/405 |
| | | | 83/348 |
| 2013/0025423 A1 | 1/2013 | Nakano | |
| 2013/0160626 A1 * | 6/2013 | Saga | B26D 7/265 |
| | | | 83/346 |
| 2013/0283987 A1 * | 10/2013 | Pras | B26D 7/22 |
| | | | 83/344 |
| 2014/0109736 A1 | 4/2014 | Schneider et al. | |
| 2017/0113365 A1 * | 4/2017 | Secondi | B26D 1/405 |

* cited by examiner

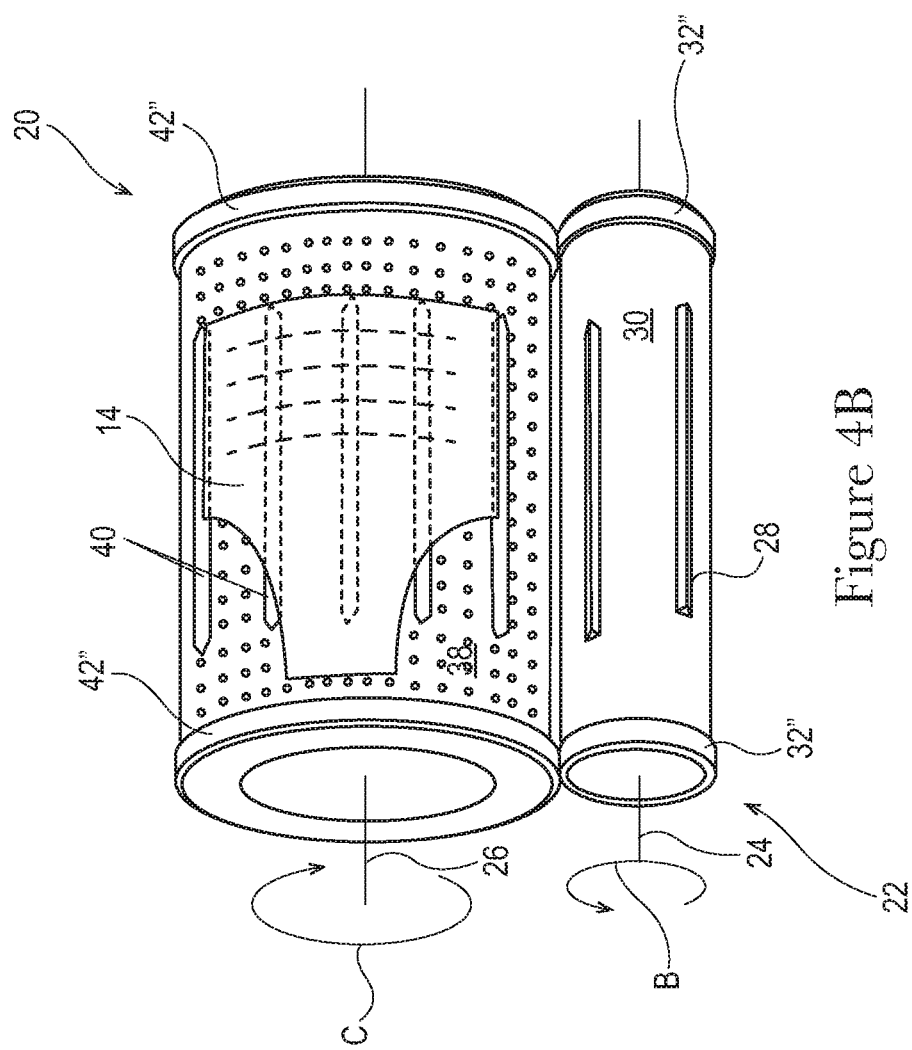

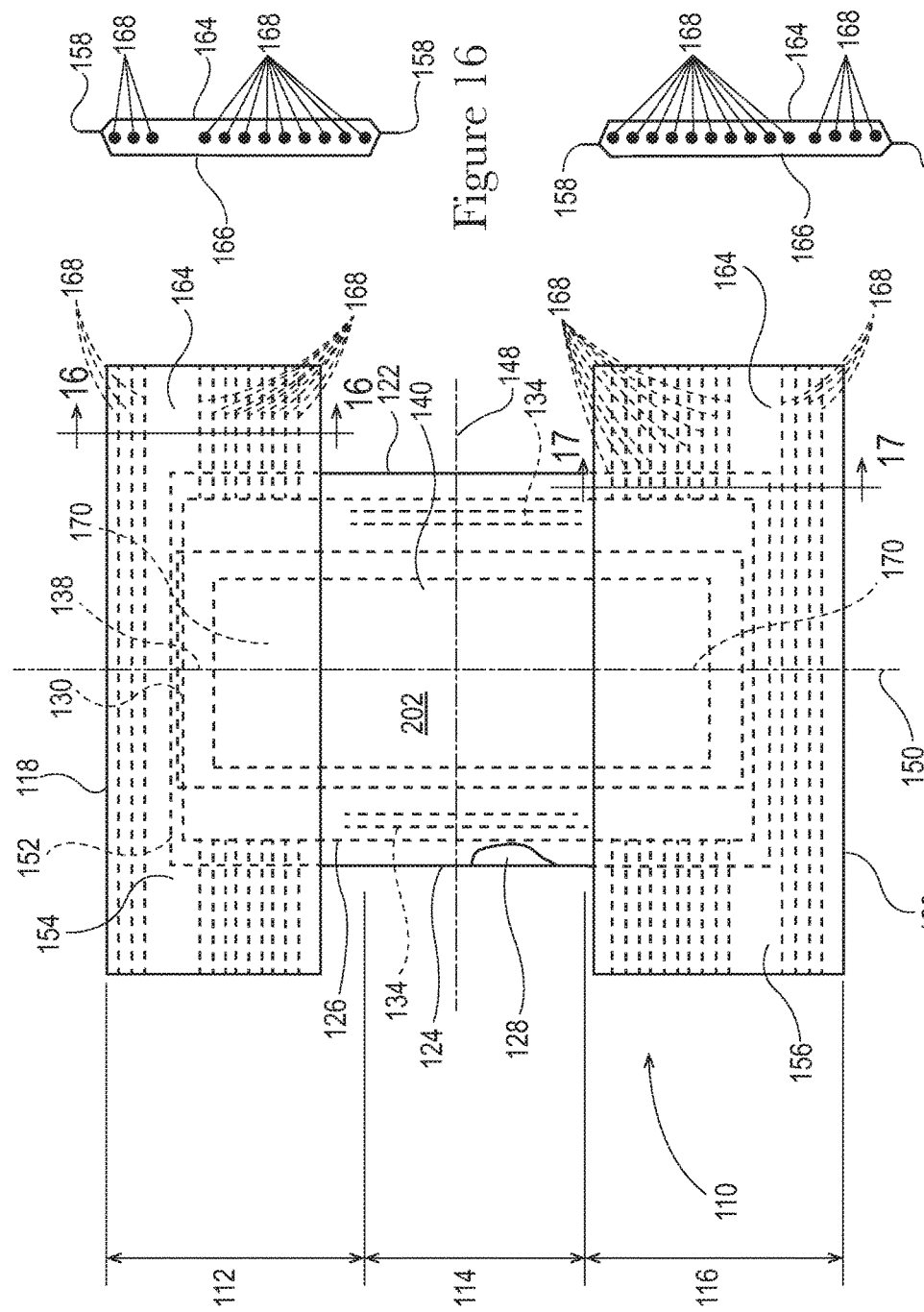

METHODS AND APPARATUSES FOR SEPARATING DISCRETE ARTICLES FROM CONTINUOUS WEBS

CROSS REFERENCE TO RELATED APPLICATION

This application claims the benefit, under 35 U.S.C. § 119(e), to U.S. Provisional Patent Application No. 62/402,129, filed on Sep. 30, 2016, which is hereby incorporated by reference in its entirety.

FIELD

The present disclosure is directed to methods and apparatuses for separating discrete articles from continuous webs.

BACKGROUND

Articles, such as absorbent articles, are sometimes produced on a continuous manufacturing line. Initially, a continuous base web may be conveyed down the manufacturing line and various components may be added to it. At the point in the manufacturing line where the articles are in final form, or a semi-finished form, it may be desirable to separate discrete articles from the continuous webs so that they can be processed for packaging or further manufacturing, for example. Typically, an anvil roll is paired with a cutting roll having a knife to cut the continuous webs. When articles, such as pants, especially larger pants (e.g., adult incontinence pants), are run through a nip between the anvil roll and the cutting roll, the articles may have a tendency to fold over themselves in various portions. This may be caused by contraction of elastics or snap-back (post-cutting) of elastics in elasticized belts of these pant articles. In other instances, this may be caused by merely the large size of the articles (e.g., bigger crotch regions outside of the cutting area). Elasticized belts and/or larger sized articles may be difficult to control with vacuum alone. Furthermore, in the conventional anvil roll/cutting roll set-up, the cutting roll and/or anvil roll is usually changed out each time a different size (or pitch) of article is desired to be cut. For example, when running a first article with a pitch (i.e., machine direction length) of 200 mm, the cutting roll and/or the anvil are usually changed out to run a second article with a pitch of 300 mm. This can lead to costly downtime. Furthermore, conventional anvil roll/cutting rolls assemblies have a problem with roll parallelism and center-to-center distances which may cause issues with cuts or separation of the continuous webs.

In view of the foregoing, methods and apparatuses for separating discrete articles from a web of the articles should be improved.

SUMMARY

The methods and apparatuses for separating discrete articles from a continuous web provided by the present disclosure overcome the disadvantages of the conventional anvil roll/cutting roll separation systems. First, one or more hold down belts are provided about portions of a radial outer surface of the anvil roll to maintain control of elastics and/or nose portions (e.g., crotch portions) of the articles, especially larger articles (e.g., adult incontinence articles). In this fashion, vacuum is not solely relied upon to hold the articles in a flat, laid out state pre- and post-cutting. In some instances, vacuum may only be turned on, or may apply a greater fluid pressure to the articles, in a separation zone. The hold down belts may reduce elastic contraction, thereby reducing portions of the articles from folding over themselves. The hold down belts may also at least partially control elastic "snap-back" post-cutting. In some instances, two hold down belts may be provided; one on each side of a separation zone or in a zone where cutting occurs.

Second, to eliminate the issue of anvil roll and cutting roll parallelism, center-to-center distances, and speed mismatches between the anvil roll and the cutting roll, the anvil roll of the present disclosure or the cutting roll of the present disclosure may be provided with a bearer ring that floats on one or more bearing members, such as bearings or a bearing surface. Thus, the floating bearer ring may be driven by the roll not comprising the bearer ring, thereby leading to high roll parallelism and center-to-center distances while also accounting for roll speed mismatches between the anvil roll and the cutting roll. The roll not comprising the floating bearer ring may comprise a fixed bearer ring configured to engage the floating bearer ring and drive it at the same speed as the driven roll not containing the floating bearer ring. The roll comprising the floating bearer ring may be independently driven relative to the floating bearer ring. This allows the roll comprising the floating bearer ring to be driven faster or slower than the floating bearer ring, thereby allowing multiple sizes of products to be cut using the same anvil roll and cutting roll, while matching the speed of the floating bearer ring with the roll without the floating bearer ring.

As an example, the present disclosure provides a system that has a floating bearer ring on the cutting roll and a fixed bearer ring on the anvil roll. The floating bearer ring is driven by the fixed bearer ring on the anvil independent of the rotational speed of the cutting roll. Therefore, the cutting roll may be rotated faster or slower than the rotation of the floating bearer ring. This allows for the cutting roll's rotation to be sped up or slowed down depending on the pitch of the article being cut, while also makes the anvil roll essentially "pitchless" since the speed of the cutting roll determines were cuts will be made. This further provides for high precision on center-to-center distances and high roll parallelism owing to the bearing rings. These two features significantly improve discrete article separation.

As another example, the present disclosure provides a cutting assembly that has multiple cutting rolls rotatably engaged with a frame, wherein a first cutting roll having a first diameter may be moved between an online position (i.e., cutting position) and a second offline position (i.e., not in a cutting position), and wherein a second cutting roll having a second, different diameter may be moved between the online position and the second offline position. Any number of cutting rolls may be provided on the frame depending on the desired cutting circumstances. The frame may be positioned proximate to the anvil roll of the present disclosure so that a first cutting roll may easily be moved from an online position to an offline position and a second, different cutting roll may be moved from an offline position to an online position, for example. This cutting assembly may be desirable when changing sizes or pitches of articles to be cut. The cutting assembly also allows for significantly reduced change out times.

BRIEF DESCRIPTION OF THE DRAWINGS

While the specification concludes with claims particularly pointing out and distinctly claiming the subject matter which is regarded as forming the present invention, it is believed that the present disclosure will be better understood from the following description which is taken in conjunction with the accompanying drawings in which the designations are used to designate substantially identical elements and in which:

FIG. 4B is another simplified example pair of rolls, including an anvil roll and a cutting roll, that may be used a component of the separation assembly of the present disclosure;

FIG. 15 is a plan view of a pant, laid flat, with a garment-facing surface facing the viewer;

FIG. 16 is a cross-sectional view of a front belt portion of the pant taken about line 16-16 of FIG. 15; and FIG. 17 is a cross-sectional view of a back belt portion of the pant taken about line 17-17 of FIG. 15.

DETAILED DESCRIPTION

Figure 1:
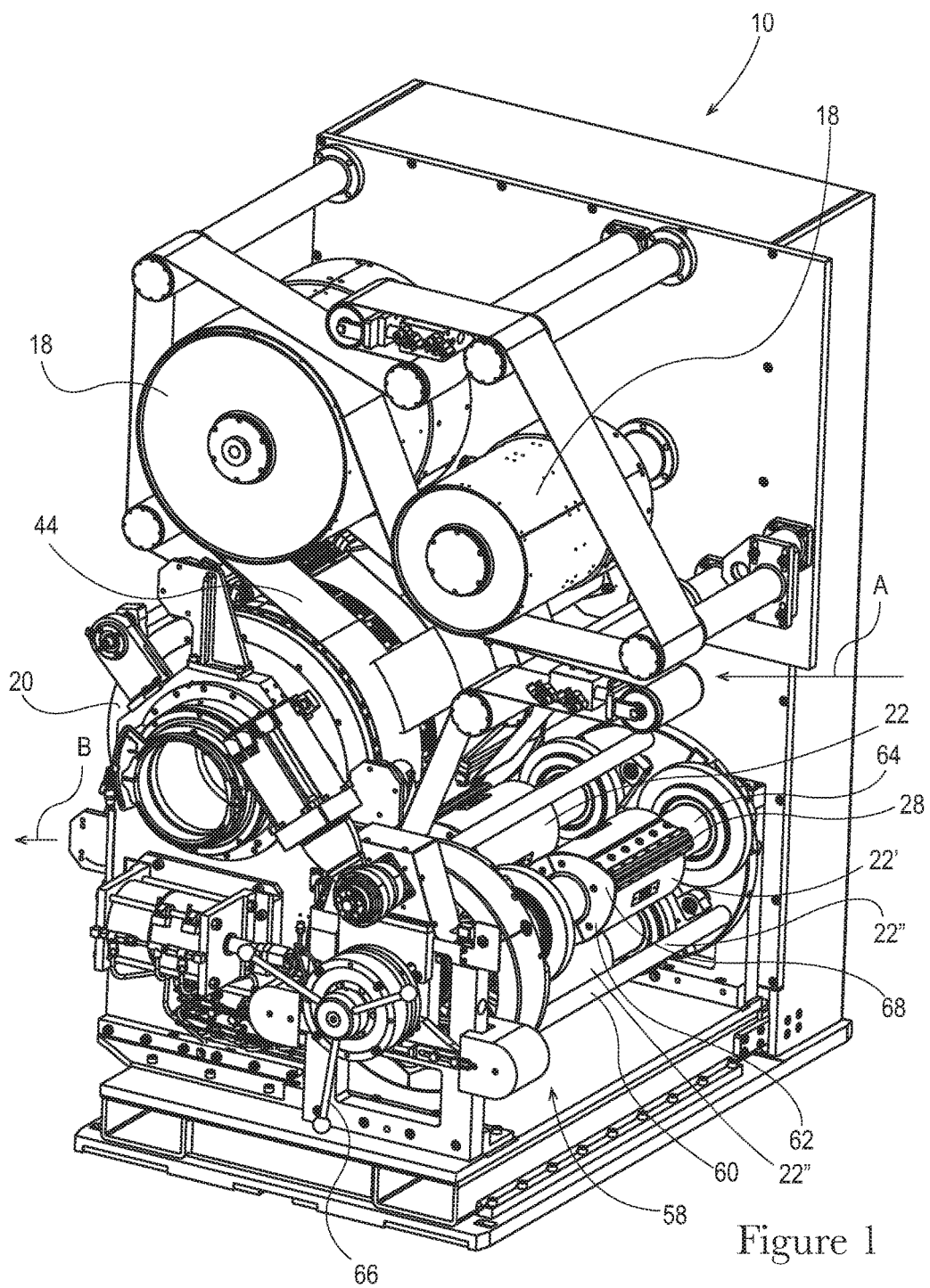
FIG. 1 is a right side perspective view of an example separation assembly of the present disclosure.

Various non-limiting forms of the present disclosure will now be described to provide an overall understanding of the principles of the structure, function, manufacture, and use of the methods and apparatuses for separating discrete articles from continuous webs disclosed herein. One or more examples of these non-limiting forms are illustrated in the accompanying drawings. Those of ordinary skill in the art will understand that the methods and apparatuses for separating discrete articles from continuous webs specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

The term "absorbent article(s)" is used herein to refer to consumer products whose primary function is to absorb and retain bodily exudates and wastes. Absorbent articles as used herein may refer to pants or adult incontinence pants, for example, or other suitable absorbent articles.

The term "machine direction" (MD) is used herein to refer to the primary direction of material, web, or article flow through a process. In various manufacturing and converting processes, such as a bi-fold process, it may be possible to have more than one machine direction when an article is undergoing simultaneous processes. In other words, a manufacturing line may have an overall machine direction, but a material or an article may travel in directions other than the overall machine direction as it passes through various processes along the manufacturing line. For example, a discrete article having a trailing end portion and a leading end portion, each portion being attached to the surface of a different roll and/or conveyor may travel in two different directions simultaneously. In this example, both directions of travel may be considered the machine direction.

The term "cross direction" (CD) is used herein to refer to a direction that is generally perpendicular to the machine direction.

The term "pant" refers herein to disposable absorbent articles having a continuous perimeter waist opening and continuous perimeter leg openings designed for infant, child, or adult wearers. A pant may be configured with a continuous or closed waist opening and at least one continuous, closed, leg opening prior to the article being applied to the wearer. A pant may be preformed by various techniques including, but not limited to, joining together portions of the absorbent article using any refastenable and/or permanent closure member (e.g., seams, heat bonds, pressure welds, adhesives, cohesive bonds, mechanical fasteners, etc.). A pant may be preformed anywhere along the circumference of the absorbent article in the waist region (e.g., side fastened or seamed, front waist fastened or seamed, rear waist fastened or seamed). A pant may be opened about one or both of the side seams and then refastened. Example pants in various configurations are disclosed in U.S. Pat. Nos. 5,246,433, 5,569,234, 6,120,487, 6,120,489, 4,940,464, 5,092,861, 5,897,545, 5,957,908, and U.S. Patent Publication No. 2003/0233082.

Figure 2:
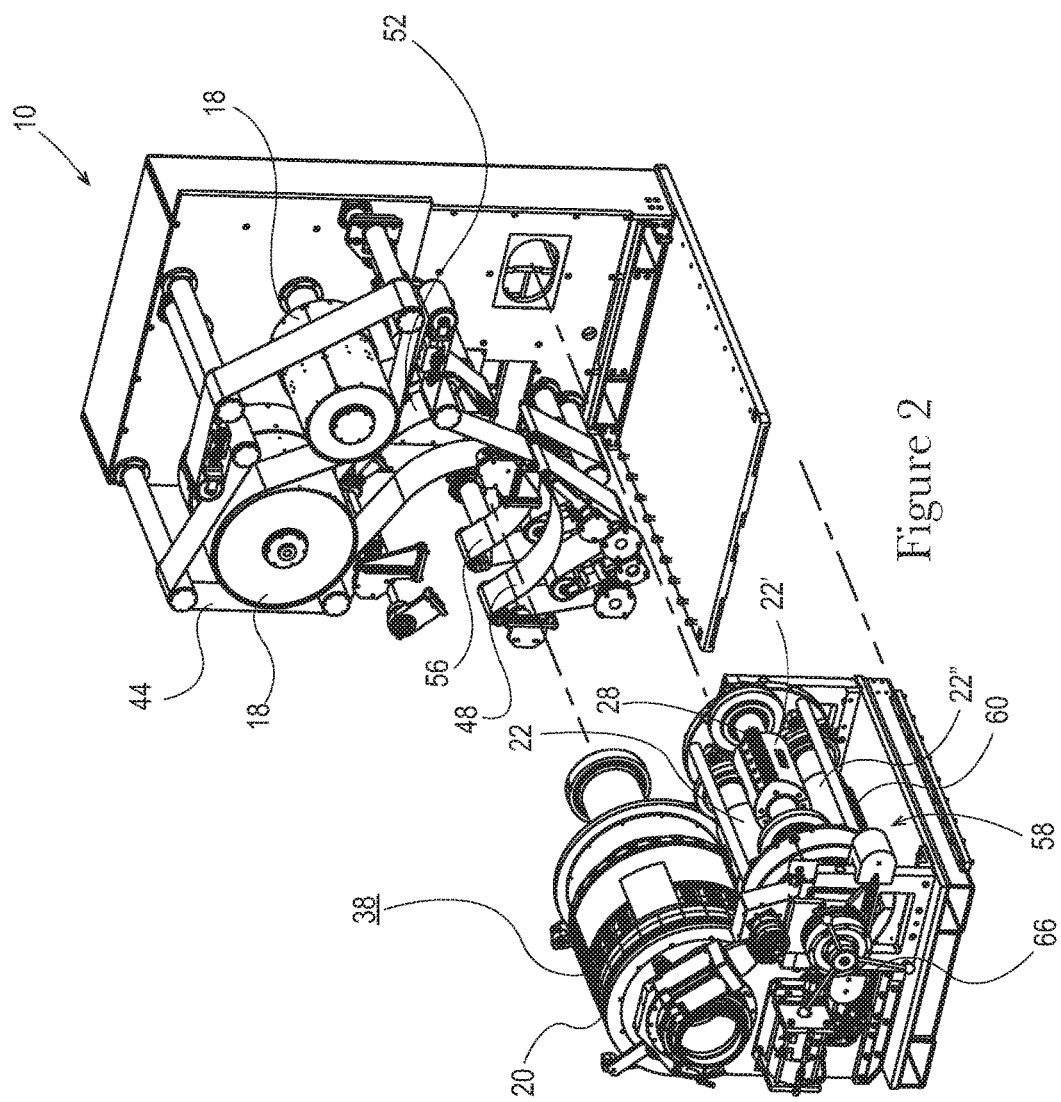
FIG. 2 is an exploded right side perspective view of the example separation assembly of FIG. 1.
Figure 3:
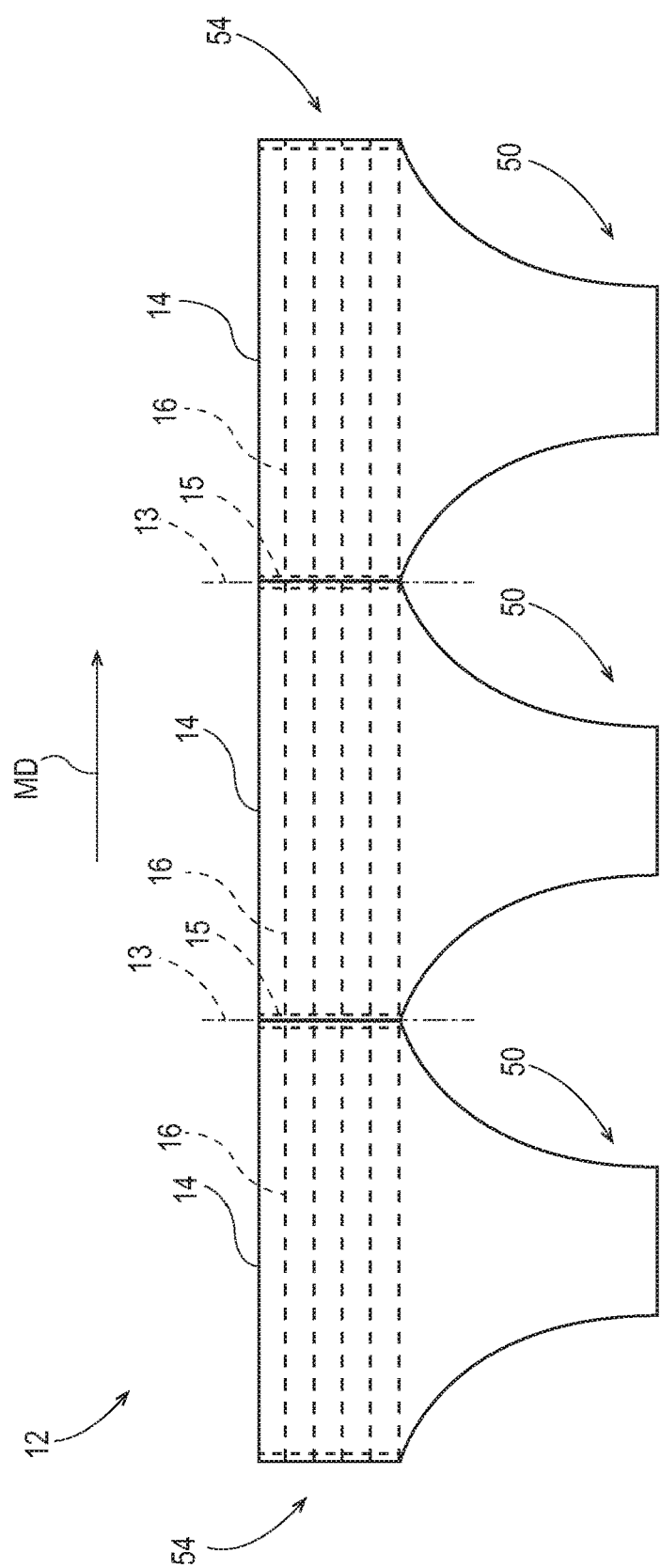
FIG. 3 is an illustration of a continuous web of articles with elastic contraction pulled-out that may be separated into discrete articles using the separation assembly of the present disclosure.

Referring to FIGS. 1 and 2, an example separation assembly 10 is illustrated. FIG. 2 is a partially separated view of the separation assembly of FIG. 1 to show additional details of the various components. The separation assembly 10 is configured to receive a continuous web at arrow A in FIG. 1 and output a plurality of discrete articles at arrow B. Referring to FIG. 3, the continuous web 12 may comprise absorbent articles 14 in the form of pants, for example. In this instance, the continuous web 12 may be conveyed toward, and partially through the separation assembly 10 in the non-separated form illustrated in FIG. 3. The continuous web 12 may then be separated by the separation assembly 10 into a plurality of discrete articles 14, at the locations indicated by dashed lines 13 in FIG. 3. The continuous web 12 is conveyed through the separation assembly 10 in the machine direction, MD (see arrow in FIG. 3). The continuous web 12 may comprise a plurality of articles 14, or absorbent articles, that have not yet been separated about their side seams. The continuous webs 12 may also comprise portions of articles, portions of absorbent articles, or other substrates in need of separation. Areas proximate to the side seams may have bonds 15 that join the front and rear portions of the articles. The separation assembly 10 is configured to separate the continuous web 12 about their side seams. Each article 14, or portion thereof, in the continuous web 12 may comprise a plurality of the elastic elements 16, such as elastic strands. These elastic elements 16 are configured to retract a waist band of the absorbent articles so that the articles can remain around a waist of a wearer. In the continuous web 12, the elastic elements 16 are continuous from one article 14 to another article 14. When the continuous web 12 is conveyed into and through the separation assembly 10, the elastic forces in the elastic elements 16 are stretched out so that the continuous web 12 lays flat on the various surfaces of the separation assembly 10. The elastic forces may be stretched out by the machine direction tension placed on the continuous web 12, for example.

Again referring to FIGS. 1 and 2, the continuous web 12, upon entering the separation assembly 10, is run over one or more drums 18 to reorient the continuous web 12 and allow the continuous web 12 to engage the anvil roll 20 far enough upstream before the separation zone 46 to allow the anvil roll 20 to gain solid control of the continuous web 12. Since pant products, especially adult incontinence pants, may be quite large when the elastic elements 16 are stretched out, it is desirable to gain adequate control of the continuous web 12 on the anvil roll 20 prior to cutting the continuous web 12 in the separation zone 46. This enables cutting at the proper locations with accurate cuts. The continuous web 12 may be controlled through the use of vacuum in the drums 18, the anvil roll 20, and/or through the use of one or more hold down belts. The hold down belts will be described in further detail below. The continuous webs 12 may also be controlled through the use of high pressure air blown towards the continuous webs 12 on the drums 18 and/or the anvil roll 20, for example. This high pressure air may be used with or without vacuum.

Figure 4:
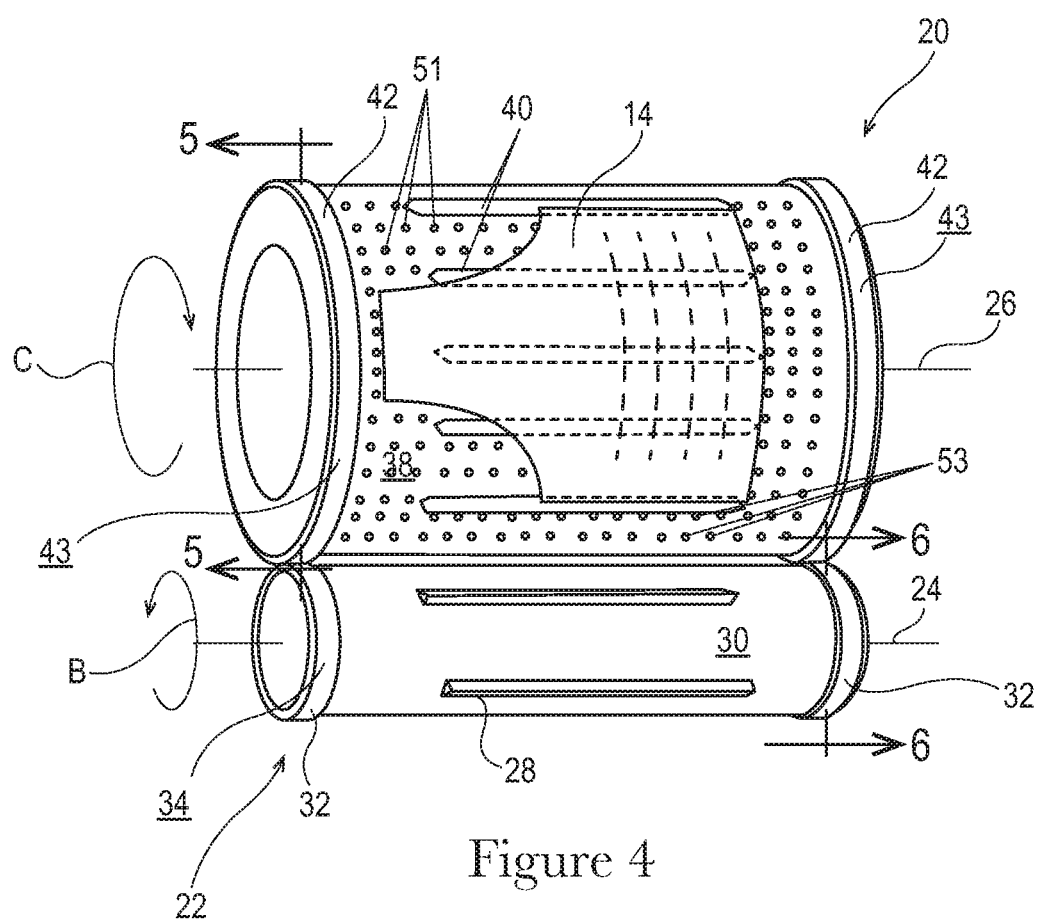
FIG. 4 is a simplified example pair of rolls, including an anvil roll and a cutting roll, that may be used as a component of the separation assembly of the present disclosure.

Referring to FIG. 4, a pair of rolls comprising an example cutting roll 22 and anvil roll 20 is illustrated. The cutting roll 22 may rotate about a first axis of rotation 24 in the direction indicated by arrow C and the anvil roll 20 may rotate about a second axis of rotation 26 in the direction indicated by arrow D. The first axis of rotation 24 may be parallel to, or generally parallel to (e.g., +/−1 degrees, +/−2 degrees, +/−3 degrees), to the second axis of rotation 26. The cutting rolls discussed herein may have the configuration illustrated in FIGS. 1 and 2, wherein the cutting roll is positioned on and fixed to a rotating drive shaft. The cutting roll 22 comprises a first radial outer surface 30. One or more cutting devices 28, such as knife bars, extend from the radial outer surface 30 of the cutting roll 22. As an example, the cutting devices 28 may have a square or rectangular cross-sectional profile, such that the four corners of the square or rectangle each may have a knife surface or cutting surface. As such, when one knife surface wears, an operator may remove the cutting device and rotate it (e.g., 90 degree rotation) such that a new, sharp knife surface is available for cutting. Here, four knife surfaces may be housed in one cutting device. Any suitable cutting devices are also within the scope of the present disclosure, including others that have different cross-sectional shapes. In FIG. 4 an example article 14 is illustrated on the anvil roll 20 to illustrate how the anvil members 40 would be aligned with the areas of the article 14 to be cut. Before contact with the cutting roll 22, although a single article is shown for illustration, a continuous web requiring separation would be present.

Figure 6:
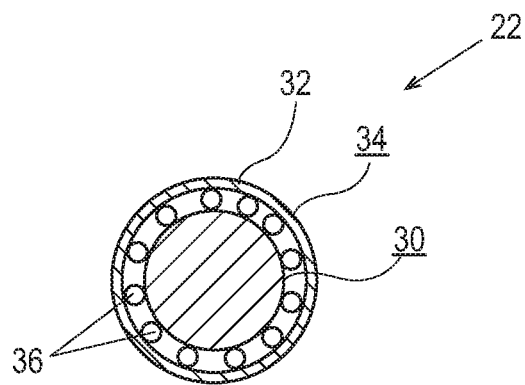
FIG. 6 is a cross-sectional example view of the cutting roll, taken about line 6-6 of FIG. 4.
Figure 6A:
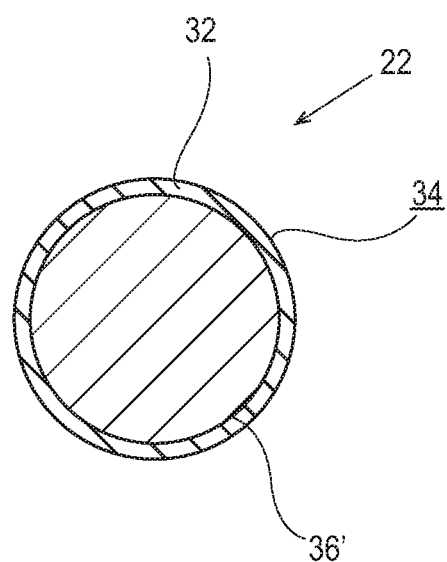
FIG. 6A is another cross-sectional example view of the cutting roll, taken about line 6-6 of FIG. 4.

Referring to FIGS. 1, 4, and 6, the cutting roll 22 may have distal portions. The distal portions may comprise bearer rings 32 extending radially outwardly from the first radial outer surface 30 (FIGS. 4 and 6) or extending more radially outwardly relative to the first axis of rotation 24 than the first radial outer surface 30 (FIG. 1). Note in FIG. 1, the bearer rings 32 do not extend radially outwardly from the first radial outer surface 30, but instead are separate from the first radial outer surface 30 on distal ends of the cutting roll 22. Here, the bearer rings 32 extending more radially outwardly, relative to the first rotation axis 24, than the first radial outer surface 30 of the cutting roll 22. The bearer rings 32, in either configuration, may extend more, or less radially, relative to the first axis of rotation 24, than the cutting devices 28. In other instances, the bearer rings 32 may extend the same, or substantially the same, distance radially, relative to the first axis of rotation 24, as the cutting devices 28.

Referring to FIGS. 1, 4, 6, and 6A, the bearer rings 32 may each comprise a second radial outer surface 34. In a first configuration, the bearer rings 32 may be fixedly attached to the first radial outer surface 30 or a portion of the cutting roll 22. In a second configuration, the bearer rings 32 may be rotatably attached to the first radial outer surface 30 or a portion of the cutting roll 22. An example of such rotatable attachment is to position bearing members, such as bearing 36 (FIG. 6) or one or more bearing surfaces 36' (FIG. 6A), for example, intermediate the first radial outer surface 30 of the cutting roll 22 or another portion of the cutting roll 22 and the surfaces of the bearer rings 32 facing the first radial outer surface 30 or facing the portion of the cutting roll 22. In such an instance, the bearer rings 32 are free to rotate about the first axis of rotation 24 of the cutting roll 22, independent of the portion of the cutting roll 22 comprising the one or more cutting devices 28. As such, the bearer rings 32 may be rotated about the first axis of rotation 24 by a portion of the anvil roll 20, as will be discussed below, at a first speed, while the portion of the cutting roll 22 comprising the one or more cutting devices 28 may be driven independently so that it rotates about the first axis of rotation 24 a second, different speed. The second, different speed may be faster or slower than the first speed. In other instances, the first and second speed may be the same. These bearer rings 32 with bearing members may be referred to herein as "floating bearer rings". The cutting devices 28 may be at least as long as the required cut length and may be positioned intermediate the bearer rings 32. In some instances, the cutting roll 22 may not comprise the bearer rings 32 and instead, a radial outer surface of a floating bearer ring on the anvil roll 20 may contact the cutting roll 22.

The anvil roll 20 rotating about the second axis of rotation 26 may comprise a third radial outer surface 38. A plurality of angularly spaced anvil members 40 may extend outwardly from the third radial outer surface 38 of the anvil roll 20. Instead of the plurality of angularly spaced anvil members 40, the anvil member may be continuous sheet or plate that surrounds the third radial outer surface 38 or forms a portion of the third radial outer surface 38, as will be described in further detail below. The anvil members 40 may be configured to receive the knife surfaces thereon to cut the continuous web 12. All of the anvil members 40, or all of the portions of the continuous anvil member, may not be contacted by a knife surface during separation of an article from the continuous web 12 depending on the article's desired pitch. If a smaller desired pitch is required, more anvil members 40 may be contacted by the knife surfaces during one revolution of the anvil roll 20. If a larger desired pitch is required, less anvil members 40 may contacted by the knife surfaces during one revolution of the anvil roll 20. The position of contact of the knife surfaces on the anvil members 40 may be adjusted across an outer portion of the anvil members 40 to evenly distribute wear on the anvil members 40. For instance, the knife surfaces may be operated to contact a leading portion of the anvil members 40 for a shift of production (e.g., 8 hours) and, then, for a second shift of production, the knife surfaces may be operated to contact a middle portion of, or another portion of, the anvil members 40 to distribute anvil member wear evenly. This adjustment may also help ensure a sufficient and clean cut between the knife surfaces and the anvil members 40. For a non-walking pitch, the knife surfaces may contact different anvil members 40 to distribute wear evenly on the various anvil members 40. The anvil members 40 may be longer than, shorter than, or the same length as, the cutting devices 28.

The anvil roll 20 may comprise distal portions (in a cross machine direction). Bearer rings 42 may be present in the distal portions and may surround the third radial outer surface 38 of the anvil roll 20. The bearer rings 42 may be fixedly attached to the third radial outer surface 38 such that the bearer rings 42 rotate in unison with the anvil roll 20 about the second axis of rotation 26. In other configurations, the bearer rings 42 may be rotatably attached to the third radial outer surface 38 such that they may be rotated independently about the second axis of rotation 26 relative to the rotation of the anvil roll 20. The bearer rings 42 may have a fourth radial outer surface 43 configured to engage the second radial outer surface 34 of the bearer rings 32.

In an example, the bearer rings 32 on the cutting roll 22 may float on one or more bearing members, such as bearings 36, while the bearer rings 42 on the anvil roll 20 may be fixedly attached to the anvil roll 20. In such an instance, the floating bearer rings 32 may be rotated independently of a driven portion of the cutting roll 20 comprising the cutting devices 28, while the fixed bearer rings 42 may rotate in unison with the anvil roll 20. When the second radial outer surface 34 of the bearer rings 32 is brought into contact with the fourth radial outer surface 43 of the bearer rings 42, the bearer rings 42 drive the rotation of the bearer rings 32. This allows for the bearer rings 32 to be rotated at the same speed as the bearer rings 42 and eliminates or reduces mismatched speed of the two sets of bearer rings, thereby reducing bearer ring wear. This also allows for independent rotational speed control of the portion of the cutting roll 22 comprising the cutting devices 28. As such, the portion of the cutting roll 22 comprising the cutting devices 28 may be rotated at a faster speed or a slower speed (or at the same speed), relative to the bearer rings 32, depending on the desired pitch of the articles being separated from the continuous web 12. The faster the cutting roll 22 is rotated, the smaller the pitch of the separated article will be. The slower the cutting roll 22 is rotated, the larger the pitch of the separated articles will be. The above two sentences assume constant speed rotation of the anvil roll 20, although the speed of rotation of the anvil roll 20 may also be varied.

In another example, the bearer rings 42 on the anvil roll 20 may float on bearing members, while the bearer rings 32 on the cutting roll 22 may be fixedly attached to the cutting roll 22. In such an instance, the floating bearer rings 42 may be rotated independent of the anvil roll 20, while the fixed bearer rings 32 may rotate in unison with the cutting roll 22. When the second radial outer surface 34 of the bearer rings 32 is brought into contact with the fourth radial outer surface 43 of the bearer rings 42, the bearer rings 32 drive the rotation of the bearer rings 42. This allows for the bearer rings 42 to be rotated at the same speed as the bearer rings 32 and eliminates or reduces mismatched speed of the two sets of bearer rings, thereby reducing bearer ring wear. This also allows for independent rotational speed control of the anvil roll 20. As such, the anvil roll 20 may be rotated at a faster speed, a slower speed, or the same speed, relative to the bearer rings 42, depending on the desired pitch of the articles being separated from the continuous web 12. The faster the anvil roll 20 is rotated, the smaller the pitch of the separated article will be. The slower the anvil roll 20 is rotated, the larger the pitch of the separated articles will be. The above two sentences assume constant speed rotation of the cutting roll 22, although the speed of rotation of the cutting roll 22 may also be varied.

In another example, the bearer rings 42 on the anvil roll 20 may float on bearing members, while the bearer rings 32 on the cutting roll 22 may also float on bearing members. In such an instance, the floating bearer rings 32 and 42 may not rotate at all when the second radial outer surface 34 of the bearer rings 32 is brought into contact with the fourth radial outer surface 43 of the bearer rings 42. In such an instance, the anvil roll 20 may rotate independently of the bearer rings 42 and the cutting roll 22 may rotate independent of the bearer rings 32. In this configuration, the bearer rings 42 on the anvil roll 20 may not rotate and the bearer rings 32 may not rotate. Here, the bearer rings 42 and 32 may be used to merely set and maintain constant the nip distance between the cutting devices 28 and the anvil surfaces or the anvil members 40.

The bearer rings 32 on the cutting roll 22 may extend a first distance from first axis of rotation, while the bearer rings 42 on the anvil roll 20 may extend a second distance from the first axis of rotation. The first distance may be the same as, greater than, or less than the second distance.

Figure 4A:
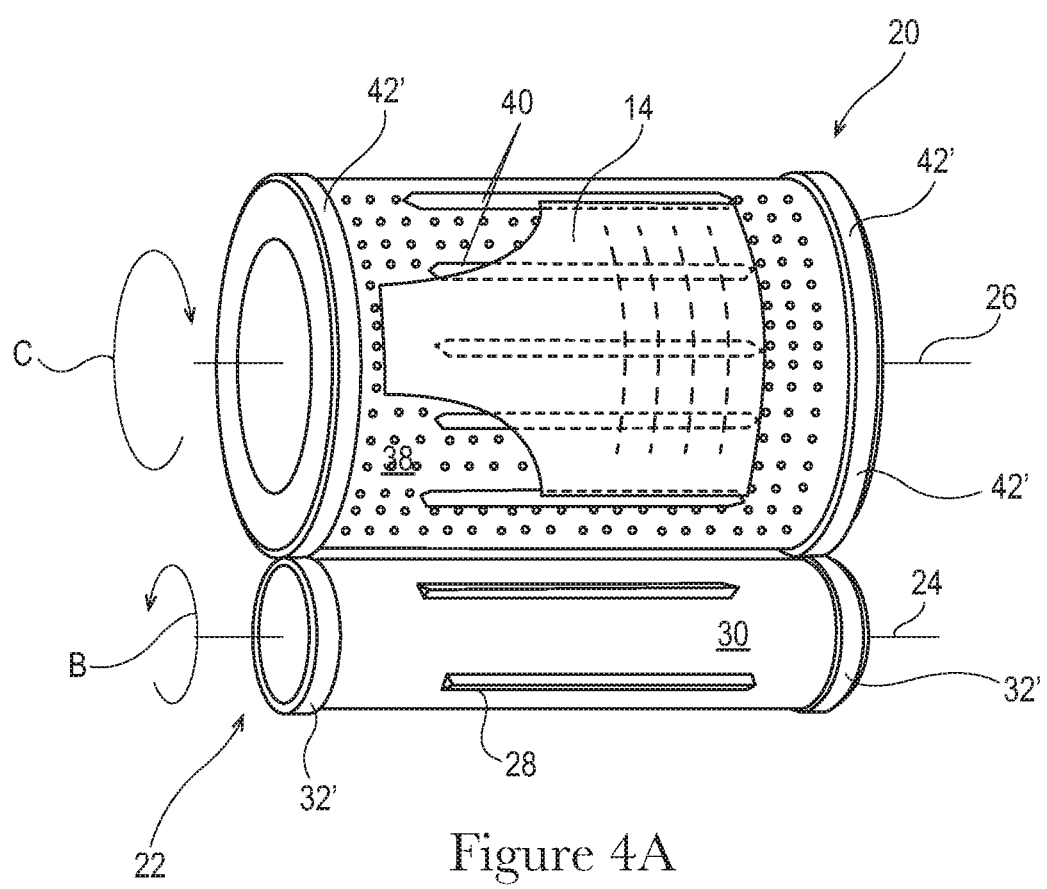
FIG. 4A is another simplified example pair of rolls, including an anvil roll and a cutting roll, that may be used a component of the separation assembly of the present disclosure.

Referring to FIG. 4A, bearing rings 42' on the anvil roll 20 may extend radially outwardly, relative to the third radial outer surface 38, from the second axis of rotation 26 further than the bearer rings 42 of FIG. 4. Bearer rings 32' on the cutting roll 22 may be radially recessed into, or from, the first radial outer surface 30 of the cutting roll 22. In such an instance, the bearer rings 42' may engage the bearer rings 32' at a location recessed with respect to the first radial outer surface 30 of the cutting roll 20. The remaining features of FIG. 4A may be the same as described with respect to FIG. 4 and are not described again here for brevity.

Referring to FIG. 4B, bearing rings 32" on the cutting roll 20 may extend radially outwardly, relative to the first radial outer surface 30, from the first axis of rotation 24 further than the bearer rings 32 of FIG. 4. Bearer rings 42" on the anvil roll 20 may be radially recessed into, or from, the third radial outer surface 38 of the anvil roll 20. In such an instance, the bearer rings 32" may engage the bearer rings 42" at a location recessed with respect to the third radial outer surface 38 of the anvil roll 20. The remaining features of FIG. 4B may be the same as described with respect to FIG. 4 and are not described again here for brevity.

Figure 4C:
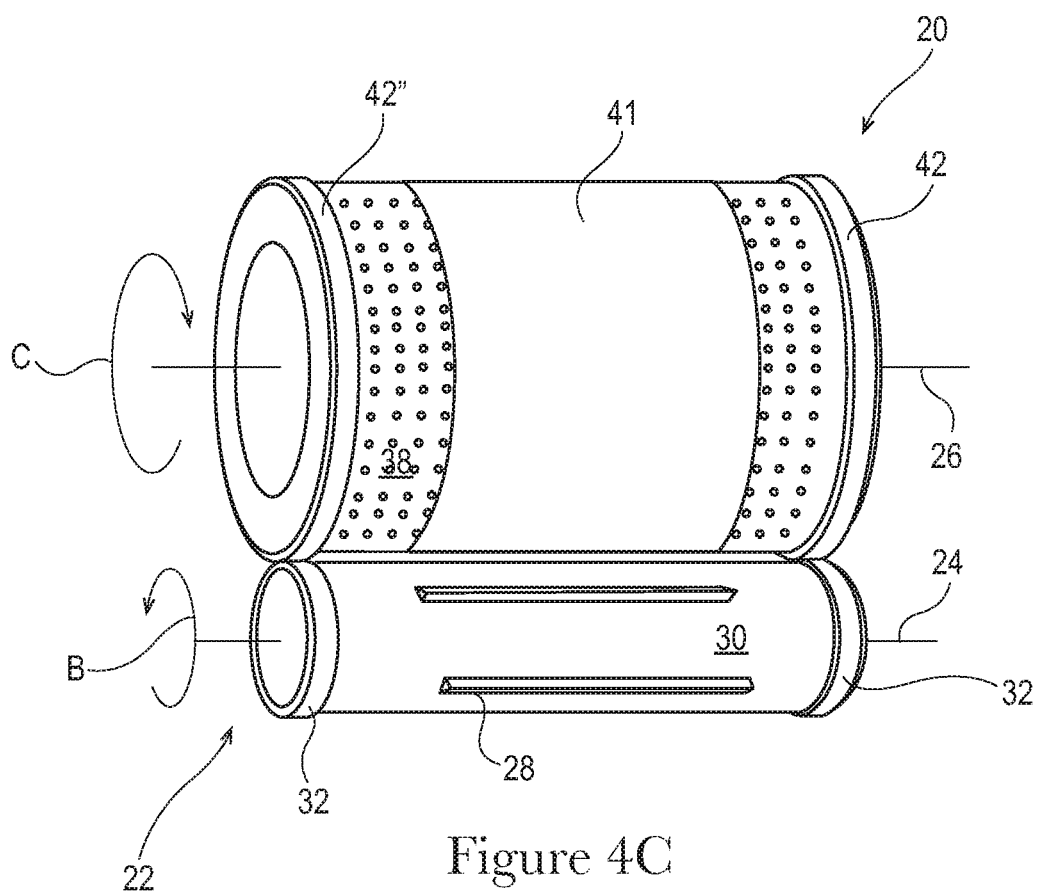
FIG. 4C is a simplified example pair of rolls, including an anvil roll and a cutting roll, that may be used as a component of the separation assembly of the present disclosure.
Figure 5:
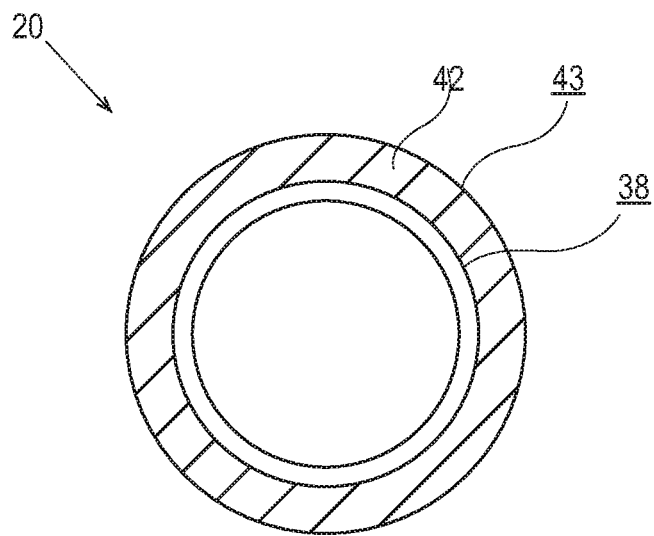
FIG. 5 is a cross-sectional example view of the anvil roll, taken about line 5-5 of FIG. 4.

Referring to FIG. 4C, the anvil surfaces may be a continuous member 41. The continuous member 41 may extending radially outwardly from a portion of the third radial outer surface 38 of the anvil roll 20, may form a portion of the third radial outer surface 38 (i.e., be flush with a portion of the third radial outer surface 38), or may be recessed with respect to a portion of the third radial outer surface 38. The continuous member 41 may fully surround, or partially surround, a portion of the anvil roll 20. The remaining features of FIG. 4C may be the same as described with respect to FIG. 4 and are not described again here for brevity. The various bearer rings may be any of those described herein.

The various bearer rings and radial outer surfaces may be referred to as the first, second third, fourth, fifth etc. in the claims depending on the order in which they are recited.

Various hold down belts that may be used in the separation assembly 10 are now discussed. These hold down belts are illustrated in FIGS. 2 and 7-9 with various components of the separation assembly 10 removed for clarity in viewing the hold down belt path. Portions of the hold down belts are also viewable in FIG. 1 without the various components removed.

Referring to FIGS. 1, 2, and 7-9, the pair of rolls comprising the anvil roll 20 and the cutting roll 22 of the separation assembly 10 may also comprise various hold down belts. The hold down belts may comprise a first hold down belt 44 on a first side of a separation zone 46 and a second hold down belt 48 on a second side of the separation zone 46. The first hold down belt 44 may wrap at least partially around the drums 18 and a portion of the anvil roll 20 on a first side of the separation zone 46. The first hold down belt 44 may be driven by the drums, separate motors, or by other suitable drive mechanisms known to those of skill in the art. The first hold down belt 44 may be configured to hold down the nose portions 50 (or bi-folded crotch regions) (see FIG. 3) of articles 14 of the continuous web 12 (pre-separation). The nose portion 50 may be sandwiched between the first hold down belt 44 and portions of radial outer surfaces of the drums 18 and a first portion of the third radial outer surface 38 of the anvil roll 20. The first hold down belt 44 may be positioned inwardly (cross machine direction) of the bearer rings 42 of the anvil roll 20, but outwardly (cross machine direction) from the cutting devices 28 of the cutting roll 22 so as to not interfere with the bearer rings 42 or be cut by the cutting devices 28. In absorbent article products, especially pant products, nose control has been a problem during processing, especially during processing through a separation assembly. This problem is sometimes exacerbated in larger absorbent article products, such as adult incontinence pants, for example, owing to their larger size. Therefore, the first hold down belt 44 is provided to maintain control of the nose portions 50 of the continuous web 12 being processed to enable improved separation of the articles and reduced nose portion fold over.

The second hold down belt 48 may be positioned on a second side of the separation zone 46. The second hold down belt 48 may function similar to the first hold down belt 44 in holding the nose portion of the articles (now separated) to a second portion of the third radial outer surface 38 of the anvil roll 20. The second hold down belt 48 may be driven by the third radial outer surface 38 of the anvil, another portion of the anvil, by separate motors, or by other suitable drive mechanisms known to those of skill in the art. The second hold down belt 48 may be positioned inwardly, in a cross machine direction, of the bearer rings 42 of the anvil roll 20 but outwardly, in a cross machine direction, from the cutting devices 28 of the cutting roll 22 so as to not interfere with the bearer rings 42 or be cut by the cutting devices 28.

Referring to FIG. 4, vacuum for the nose portions 50 may be provided through fluid ports 51 defined through a portion of the third radial outer surface 38 of the anvil roll 20 at least in the separation zone 46 to maintain the nose portions 50 in a flat, laid out position on the third radial outer surface 38 of the anvil roll 20. Stated another way, vacuum may be provided through the fluid ports 51 in the anvil roll 20 at least intermediate the first and second hold down belts 44 and 48 to maintain control of the nose portions 50 through the separation zone 46. Vacuum may be provided through the fluid ports 51 using any fluid movement systems known to those of skill in the art. This vacuum may be provided anywhere the nose portions 50 contact the third radial outer surface 38 in some instances and not just in the separation zone 46. High pressure air may be blown toward the anvil roll 20 in various locations to maintain the continuous web 12 against the third radial outer surface 38. The high pressure air may be used with or without vacuum.

Again referring to FIG. 4, vacuum may also be provided through fluid ports 53 defined in a portion of the radial outer surface 38 of the anvil roll 20. This vacuum may be configured to maintain the elastic belts 54, and potentially other portions of the continuous web (or separated articles), in a flat, laid-out state and prevent, or at least inhibit, elastic contraction and fold over in portions of the elastic belts 54. The vacuum may be provided through the fluid ports 53 using any fluid movement systems known to those of skill in the art. This vacuum may be provided anywhere the continuous web 12 or the separated articles 10 contact the radial outer surface 38 of the anvil roll 20 or may only be provided in or in and around the separation zone 46. Again, here, high pressure air may be blown toward the anvil roll 20 in various locations to maintain the continuous web 12 against the third radial outer surface 38. The high pressure air may be used with or without vacuum.

In addition to the fluid ports 51 and 53 being used to supply vacuum, they may also be used for providing a positive fluid pressure, known as "blow off". The fluid ports 51 and 53 may be supplied with this positive pressure when the discrete articles 14 are being transferred off of the anvil roll 20 to a further processing step.

In an instance, only one hold down belt may be provided and that hold down belt may be on the first side of the separation zone 46, may be on a second side of the separation zone 46, or may extend from the first side of the separation zone 46, through the separation zone 46, and to the second side of the separation zone 46. In another instance, the first and second hold down belts 44 and 48 may be provided on opposite sides of the separation zone 46 and a third hold down belt may be provided in or across the separation zone 46 to maintain control of the articles within the separation zone 46 during cutting.

Figure 7:
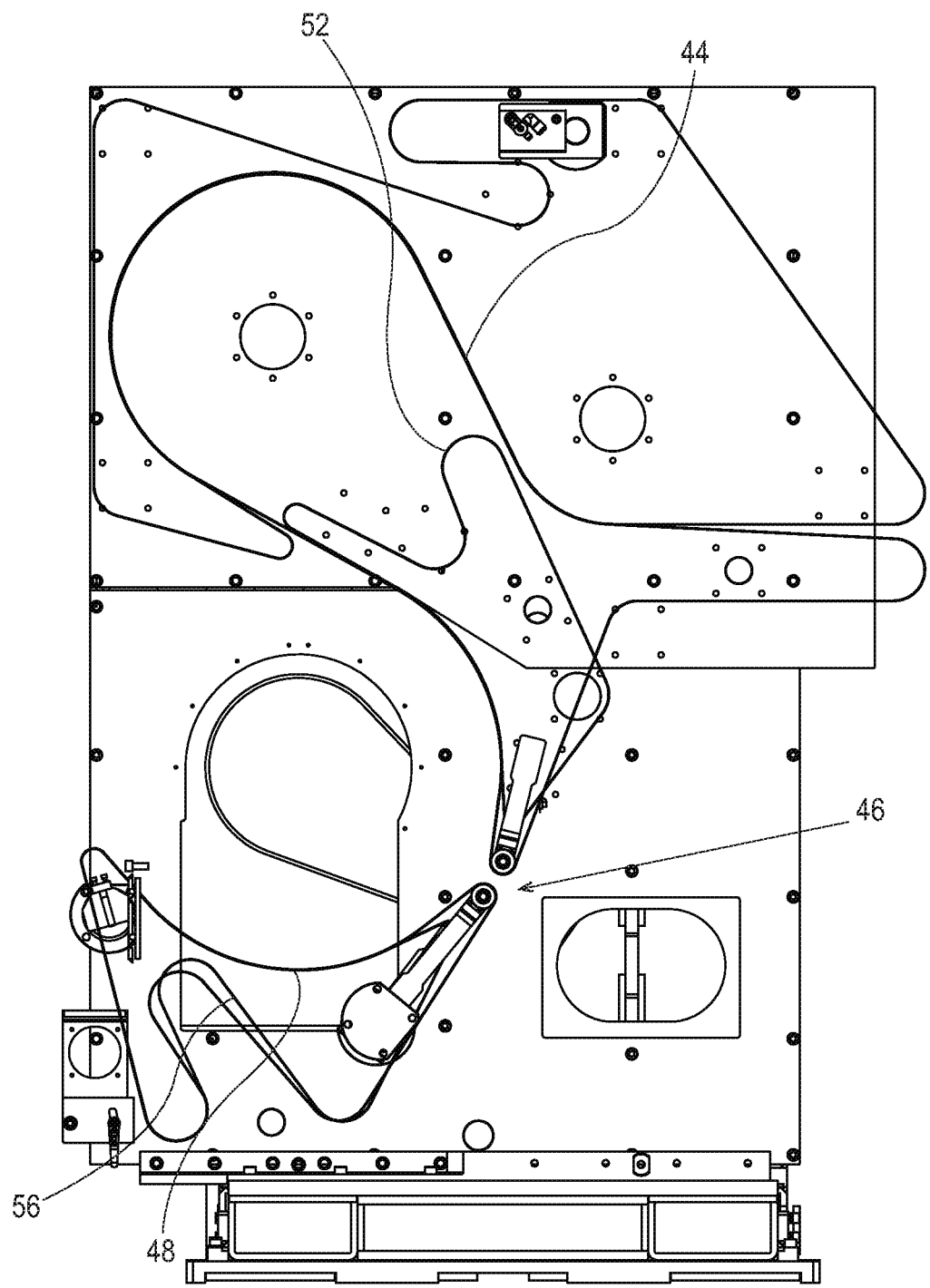
FIG. 7 is a front view of the separation assembly of the present disclosure showing an example hold down belt path, with various components of the separation assembly removed for clarity.
Figure 8:
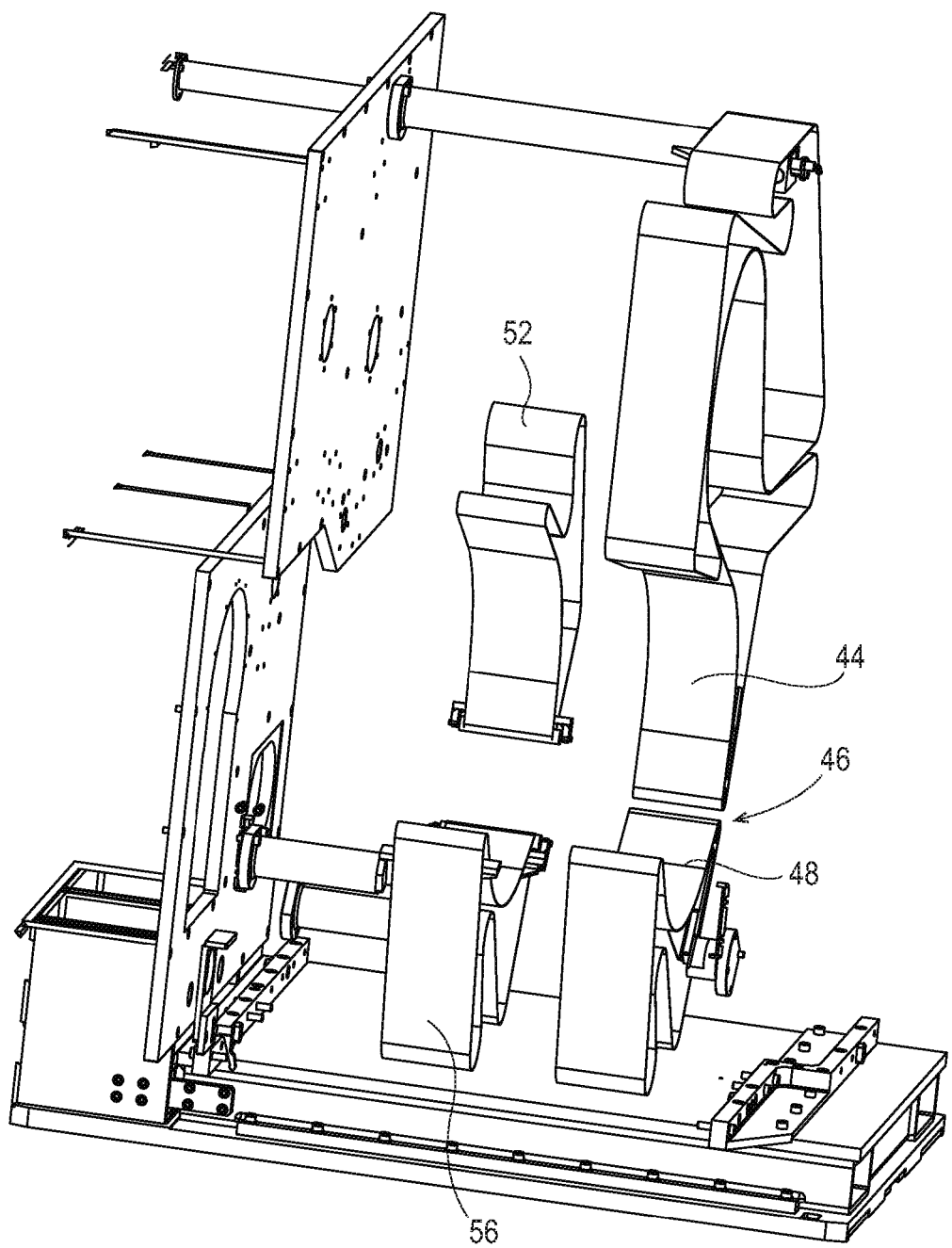
FIG. 8 is a left side perspective view of the hold down belt path of FIG. 7.
Figure 9:
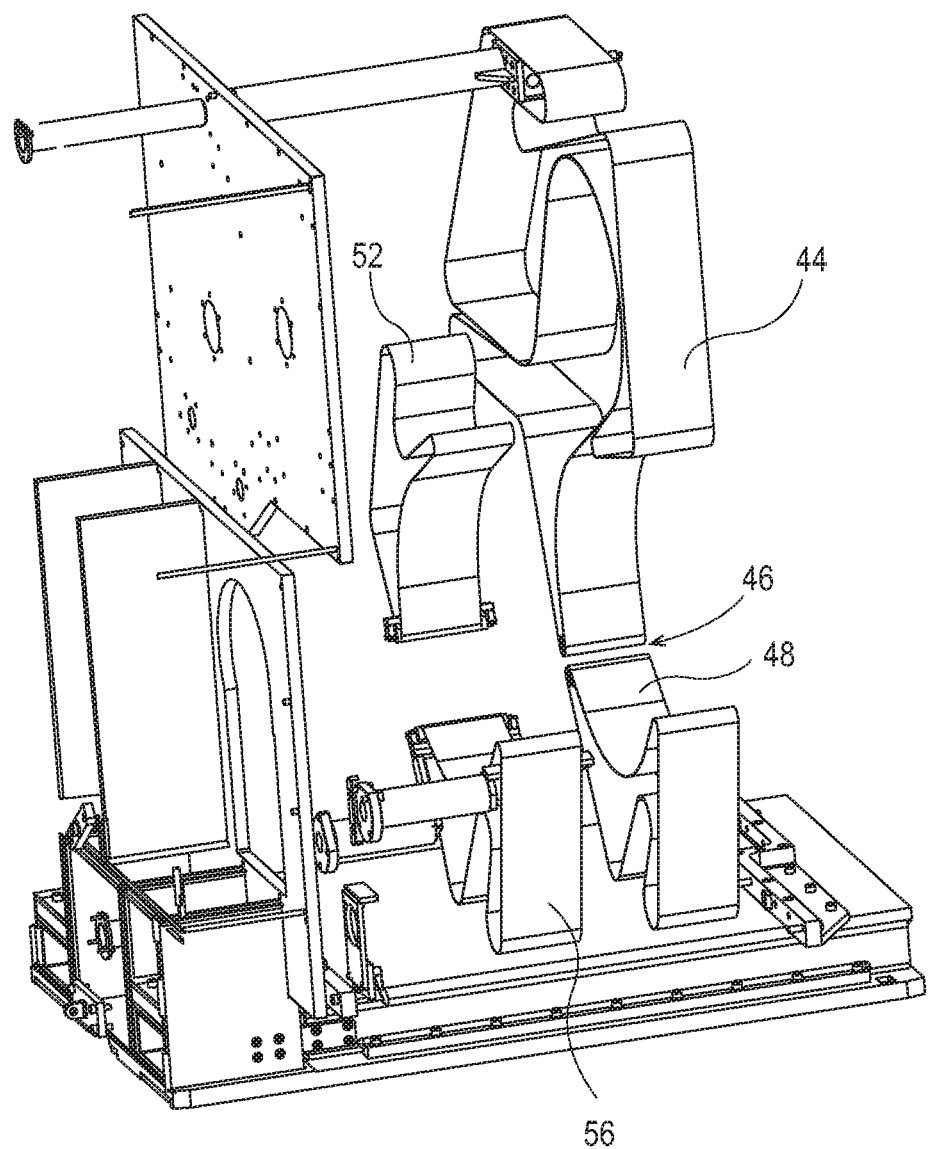
FIG. 9 is another left side perspective view of the hold down belt path of FIG. 7.

Referring to FIGS. 7-9, a third hold down belt 52 may be provided on a first side of the separation zone 46. The elastic belts 54 (see FIG. 3) of the continuous web 12 may be sandwiched between the third hold down belt 52 and a first portion of the third radial outer surface 38 of the anvil roll 20 on the first side of the separation zone 46. The third hold down belt 52 may be driven by the radial outer surface 38 of the anvil roll 20, by separate motors, or by other suitable drive mechanisms known to those of skill in the art. The third hold down belt 52 may help maintain the elastics belts 54 in a stretched out, flat state before the articles 14 are separated from the continuous web 12 in the separation zone 46. Controlling these elastic belts 54 before separation is important to achieve accurate cutting and preventing, or at least inhibit, portions of the continuous web 12 from folding over themselves. Controlling the elastic belts 54 is also important to maintain the noses 50 in position and to prevent, or at least inhibit, elastic element 16 snap-back post-separation.

A fourth hold down belt 56 may be provided on a second side of the separation zone 46. The elastic belts 54 (see FIG. 3) of the separated articles 14 may be sandwiched between the third hold down belt 52 and a second portion of the third radial outer surface 38 of the anvil roll 20 on the second side of the separation zone 46. The fourth hold down belt 56 may be driven by the radial outer surface 38 of the anvil roll 20, by separate motors, or by other suitable drive mechanisms known to those of skill in the art. The fourth hold down belt 56 may help reduce elastic "snap-back" after the articles 14 are separated from the continuous web 12 in the separation zone 46. Controlling these elastic belts 54 after separation is important for proper processing of the articles to prevent, or at least inhibit, portions of the elastics belts 54 from folding over themselves or other portions of the articles. Controlling the elastic belts 54 is also important to maintain the noses 50 in position and to prevent, or at least inhibit, elastic element 16 snap-back post-separation.

Any of the various hold down belts may comprise belt tensioners to maintain tension in the belt, as is generally known to those of skill in the art. In the claims, the hold down belts may be referred to as the first, second third, fourth etc. depending on the order in which they are referred to.

In some instances, the pair of rolls comprising the anvil roll 20 and the cutting roll 22 of the separation assembly may be used without one or more of the above described hold down belts.

It may be desirable for the separation assembly to have more than one cutting roll, such as two, three, four, or five cutting rolls, for example. Multiple cutting rolls are illustrated in FIGS. 1 and 2. The various cutting rolls may be mounted on a frame positioned adjacent to the anvil roll 20. The cutting rolls may have different diameters to cut different pitches of articles 14 in conjunction with the anvil roll 20 from the continuous web 12. In some instances, two or more of the cutting rolls may have the same diameter such that one may be used as a spare, for example. The multiple cutting rolls may be the same as the cutting roll 22, with the exception, in some instances, of diameter differences. By providing multiple cutting rolls, the same anvil roll may be used, in conjunction with one of the cutting rolls, to cut different pitches of articles without change-outs. Stated another way, the separation assembly may essentially be "pitchless" or not limited to only cutting one pitch of articles.

Figure 10:
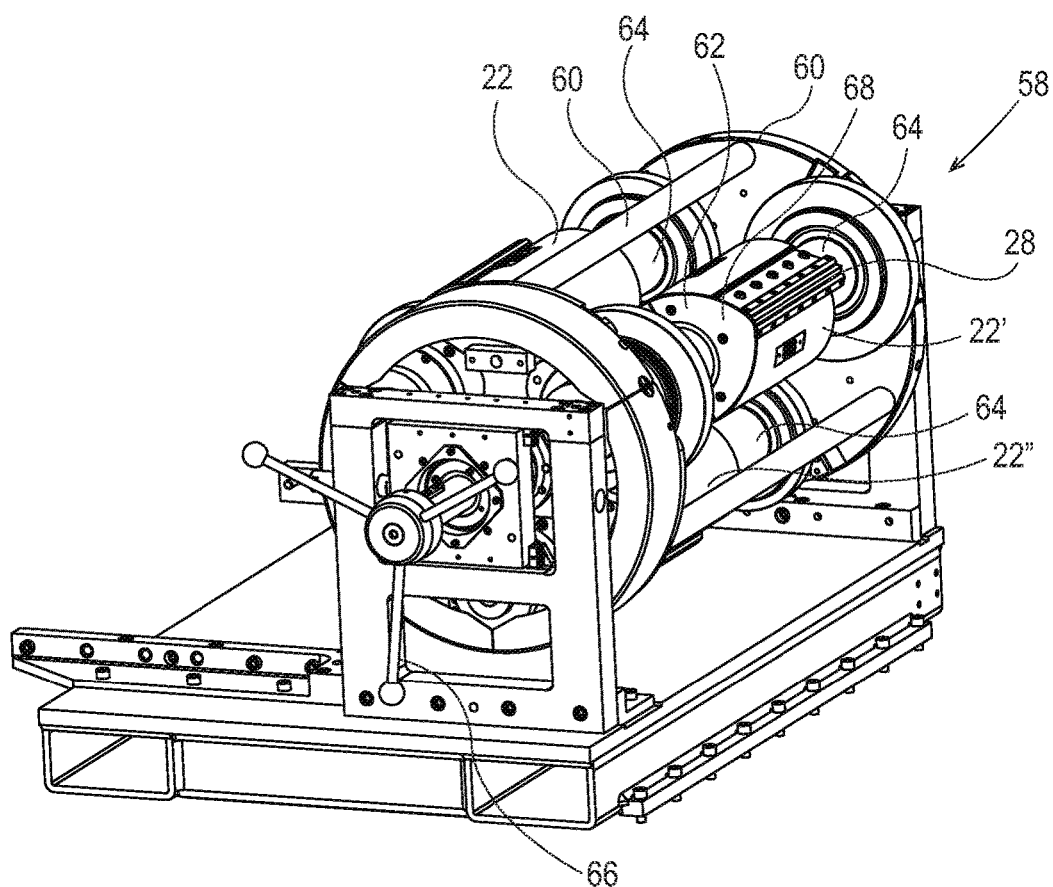
FIG. 10 is a perspective view of a cutting assembly of the separation assembly of FIG. 1.
Figure 11:
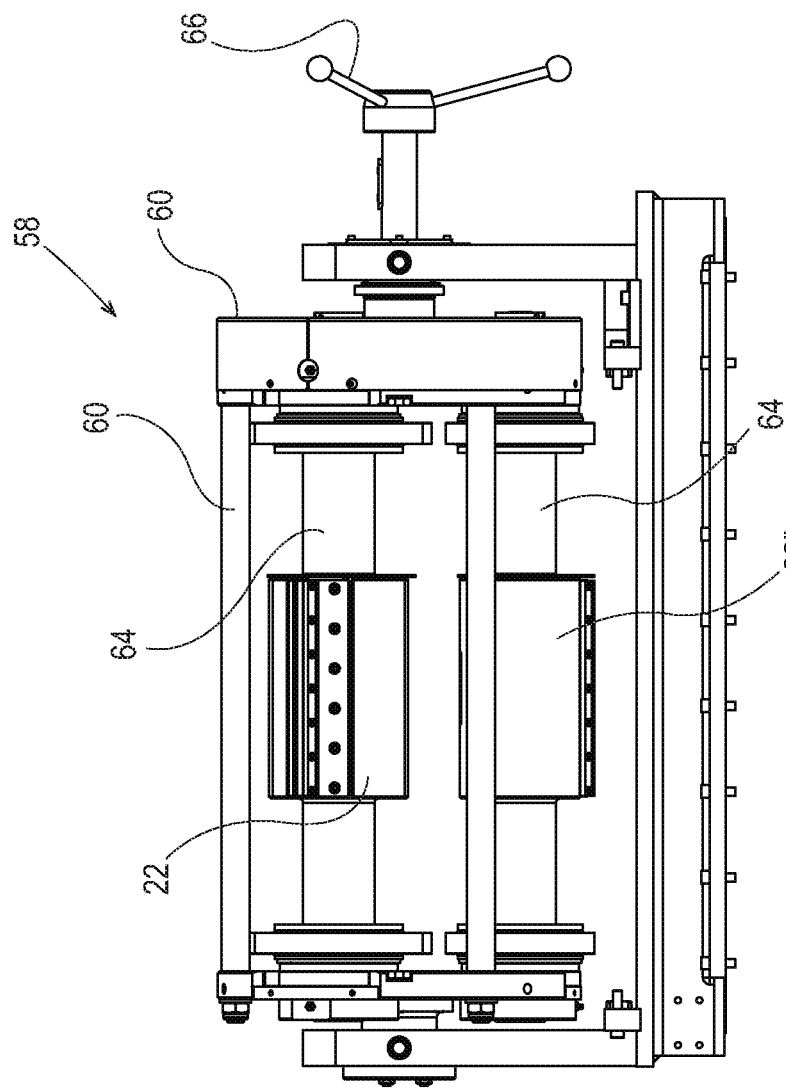
FIG. 11 is a front view of the cutting assembly of FIG. 10.
Figure 12:
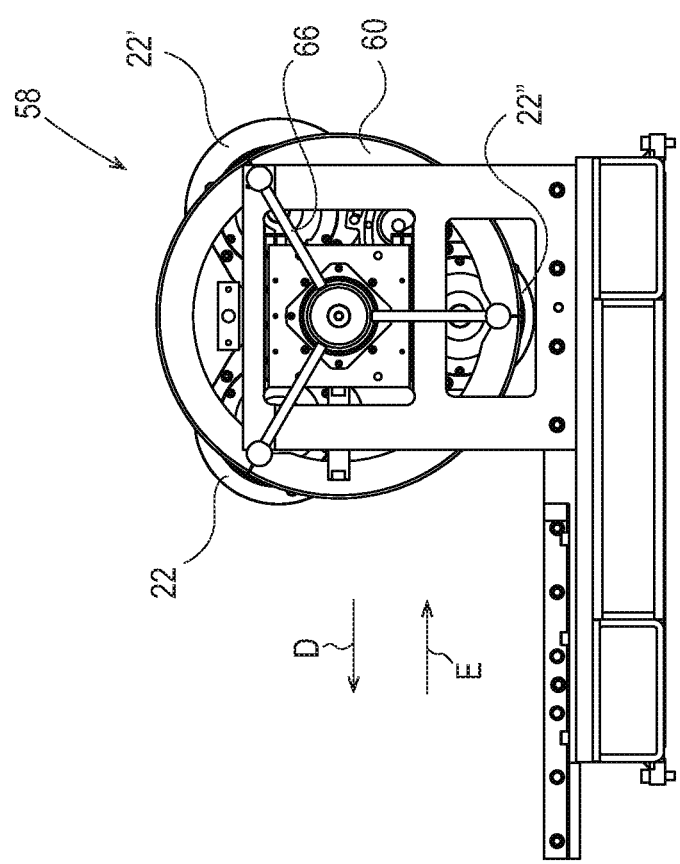
FIG. 12 is a left side view of the cutting assembly of FIG. 10.

Referring to FIGS. 1, 2, and 10-12 multiple cutting rolls 22, 22', 22", mounted on a frame 60 may be referred to as cutting assembly 58. FIGS. 10-12 illustrate views of the cutting assembly 58 with various pieces of the separation assembly 10 removed for clarity. The cutting assembly 58 may comprise a first cutting roll 22, a second cutting roll 22', and a third cutting roll 22". In one example, the cutting rolls 22, 22', and 22" may be positioned 120 degrees apart from each other, or other degrees apart from each other. Each of the cutting rolls may be rotatably positioned on the frame 60 and may comprise one or more cutting devices, like the cutting devices 28 described above. At least one of the first, second, and third cutting rolls 22, 22', and 22", or the portions comprising the cutting devices 28, may have a different diameter than the remaining cutting rolls. All of the cutting rolls 22, 22', and 22", or the portions comprising the cutting devices 28, may have different diameters. In this instance, the cutting rolls 22, 22', and 22" may each be used to cut at different article pitches. All of the cutting rolls 22, 22', and 22", or the portions comprising the cutting devices 28, may have the same diameters. In this instance, the cutting rolls 22, 22', and 22" may be used to cut at the same article pitches, such that two of the cutting rolls may be used as spares. A drive mechanism, such as a motor driving a continuous belt may be used to rotate the cutting rolls. The belt may be operably engaged with drive shafts 64 of each of the cutting rolls such that the movement of the belt transmits rotational energy to the drive shafts 64, which thereby rotates the various cutting rolls. Portions of the cutting rolls 22, 22', 22" comprising the cutting devices 28 may be fixed to the drive shafts 64 so that they rotate in unison with the drive shafts 64. In other instances, a motor may be operably engaged with each drive shaft to rotate each respective drive shaft, and thereby each respective cutting roll, independently. The portions of the cutting rolls 22, 22' and 22" comprising the cutting devices 28 may have different diameters, while the drive shafts 64 may have the same, or substantially similar, diameters. This allows the drive shafts 64 to all be driven by the drive mechanism at the same surface speed but causes the portions of the cutting rolls comprising the cutting devices to be driven at different surface speeds, owing to their differing diameters.

Referring to FIGS. 1, 2, and 10, the various cutting rolls may each comprise an elongated plate 62 having one or more elongated portions 68. The elongated plate 62 may have a guitar pick-like shape, with the elongated portion 68 in general alignment with a cutting device 28. The elongated plate 62 is positioned intermediate one of the bearer rings 32 on the cutting roll 22 and the portion of the cutting roll 22 comprising the one or more cutting device 28. The elongated plate 62 may be fixedly attached to the cutting roll 22, so that elongated plate 62 rotates in unison with the cutting roll 22. The elongated portion 68 extends more radially outwardly than the remainder of the elongated plate 62 relative to the first axis of rotation 24. The various hold down belts may have a tendency to "walk". Walk is movement of a belt in the cross-machine direction during rotation of the belt. The elongated portion 68 acts to prevent, or at least inhibit, the cutting device 28 from cutting one of the hold down belts. If more than one cutting device is provided on a single cutting roll, the elongated plate 62 may have an elongated portion 68 corresponding to each cutting device to again ensure that the cutting devices do not cut the hold down belts.

The various cutting rolls may be moved into and out of an online position with the anvil roll 20 through the use of a shifter. Stated another way, one cutting roll may be moved from a position in which it is proximate to the anvil roll 20 to accomplish separation of the continuous web 12 to a position in which it is distal from the anvil roll 20 and does not accomplish separation. For example, the first cutting roll 22 may be moved from an online position to an offline position and then (or at the same time) the second cutting roll 22' may be moved from an offline position to an online position. The shifter, for example shifter 66, may rotate the cutting rolls in a clockwise or counter-clockwise direction with respect to the frame 60 to achieve such movement. In one example, the shifter may be rotated to move each cutting roll about 120 degrees in a clockwise or counter-clockwise direction to achieve movement of one cutting roll from the online position to an offline position and, at the same time, to achieve movement of another cutting roll from the offline position into an online position. If two cutting rolls are provided in the cutting assembly, the shifter 66 may be rotated about 180 degrees, for example. If four cutting rolls are provided in the cutting assembly, the shifter 66 may be rotated about 90 degrees, for example. In other instances, the shifter may be a linear shifter or other suitable shifter. The shifter may be configured to move the second cutting roll 22' between an online position and an offline position and then (or at the same time) move the first or third cutting rolls 22, 22", respectively, between an offline position into an online position. The shifter and multiple cutting rolls of the cutting assembly allows for very fast change over from cutting at a first article pitch to a second or third (fourth, fifth etc.) article pitch. In other instances, the cutting rolls may all be the same (e.g., spares), and they may be shifted into an out of the online position as the various cutting devices wear out. Any other type of shifter is also within the scope of the present disclosure. Once the cutting rolls on the frame are in the desired position, they may be locked in place with for example, a latch, locking pin, and/or a braking mechanism, for example.

Referring to FIG. 12, at the time when it is desired to change which cutting roll is cooperating with the anvil roll 20 for separation, the cutting assembly 58 may be moved away from the anvil roll 20 in the direction of arrow D. The shifter 66 may then be used to reposition the appropriate cutting device and then the cutting assembly 58 may be moved back toward the anvil roll 20 in the direction of arrow E. This movement of the cutting assembly 58 may be accomplished by having the cutting assembly 58 on tracks, for example. The movement may be accomplished by the use of one or more actuators, one or more linear actuators, or by human movement, for example. One the cutting assembly 58 is positioned proximate to the anvil roll 20, the cutting assembly 58 may be locked in place using a latch, a locking pin, and/or a braking mechanism, for example. The position of the anvil roll 20 and a cutting roll 22 of the cutting assembly 58 may be set by bearer rings. The bearer rings allows for high anvil roll 20/cutting roll 22 parallelism and center-to-center distance accuracy. The bearer rings provide accurate distance setting between the various cutting devices and the anvil surfaces and/or the anvil members 40.

Example methods of separating discrete articles from a continuous web of discrete articles are now described. The various components (e.g., rolls, bearer rings, surfaces) may be referred to as first, second, third etc. depending on the order in which the components are referred to herein and the in claims.

A method of separating discrete articles from a continuous web or a continuous web of article is provided. The method may comprise providing a cutting roll comprising a first axis of rotation, a first radial outer surface, and a cutting device extending radially outwardly, relative to the first axis of rotation, from the first radial outer surface. The method may comprise providing a bearer ring on the cutting roll that extends more radially outwardly than the first radial outer surface of the cutting roll relative to the first axis of rotation. The bearer ring comprises a second radial outer surface. The method may comprise providing a bearing member positioned at least partially intermediate a portion of the cutting roll and the bearer ring. The bearer ring may be configured to rotate about the first axis of rotation independent of the cutting roll. The method may comprise providing an anvil roll comprising a second axis of rotation, a third radial outer surface, and a plurality of angularly spaced anvil surfaces on, or extending radially outwardly from, the third radial outer surface. The method may comprise positioning the anvil roll and the cutting roll such that the first axis of rotation is generally parallel to the second axis of rotation, and such that the second radial outer surface of the bearer ring is in contact with a portion of the anvil roll. The method may comprise rotating the anvil roll about the second axis of rotation, using the anvil roll to drive the bearer ring about the first axis of rotation at a first speed, and rotating the cutting roll at a second, different speed about the first axis of rotation independent of the anvil roll and the bearer ring. The method may comprise conveying the web intermediate the anvil roll and the cutting roll and separating a discrete article from the continuous web by cutting the continuous web intermediate one of the plurality of anvil surfaces and the cutting device in a separation zone. The plurality of anvil surfaces may be formed on an anvil surface surrounding a portion of the anvil roll or surrounding a portion of the third radial outer surface. Alternatively, the plurality of anvil surfaces may comprise a plurality of angularly spaced anvil members. These anvil members may extend radially outwardly, relative to the second axis of rotation, from the third radial outer surface of the anvil roll. The bearing member may comprise a plurality of bearings and/or may comprise a bearing surface. The bearer ring may surround a portion of the first radial outer surface of the cutting roll.

The method may comprise providing a second bearer ring surrounding a portion of the anvil roll. The second bearer ring may have a fourth radial outer surface. The fourth radial outer surface of the second bearer ring may be in contact with the second radial outer surface of the bearer ring on the cutting roll.

The method may comprise providing at least a second cutting roll comprising a third axis of rotation, a fourth radial outer surface, and a second cutting device extending radially outwardly, relative to the third axis of rotation, from the fourth radial outer surface. The method may comprise providing a second bearer ring on the second cutting roll. The second bearer ring may extend more radially outwardly than the fourth radial outer surface of the cutting roll. The second bearer ring may comprise a fifth radial outer surface. The method may comprise providing a second bearing member positioned at least partially intermediate a portion of the cutting roll and the second bearer ring. The second bearer ring may be configured to rotate about the third axis of rotation independent of second cutting roll. The method may comprise moving the cutting roll a distance from the anvil roll such that the cutting roll is not in contact with the anvil roll. The method may comprises positioning the anvil roll and the second cutting roll such that the second axis of rotation of the anvil roll is generally parallel to the third axis of rotation of the second cutting roll, and such that the fifth radial outer surface of the second bearer ring is in contact with a portion of the anvil roll. The method may comprise rotating the anvil roll about the second axis of rotation and using the anvil roll to drive the second bearer ring about the third axis of rotation at a third speed. The method may comprise rotating the second cutting roll at a fourth speed about the third axis of rotation independent of the anvil roll and the second bearer ring, conveying a second continuous web intermediate the anvil roll and the second cutting roll, and separating a second discrete article from the second continuous web by cutting the second continuous web intermediate one of the plurality of anvil surfaces and the second cutting device. The method may comprise providing a third bearer ring surrounding a portion of the anvil roll. The third bearer ring may have a sixth radial outer surface. The sixth radial outer surface of the second bearer ring may be in contact with the fifth radial outer surface of the bearer ring on the second cutting roll. The second discrete article may have a different pitch than the discrete article. The cutting roll may have a different or the same diameter than the second cutting roll. The method may comprise rotating the cutting roll about the first axis of rotation independent of the anvil roll and the bearer ring at a first, constant angular velocity before the moving step and rotating the second cutting roll about the third axis of rotation independent of the anvil roll and the second bearer ring at a second, different, constant angular velocity after the moving step.

The method may comprise providing a first hold down belt on a first side of the separation zone. The first hold down belt may be offset in a cross-machine direction from the cutting device. The method may comprise moving the first hold down belt over a first portion of the third radial outer surface of the anvil roll and using the first hold down belt to hold portions of the continuous web against the first portion of the third radial outer surface. The method may comprise providing a second hold down belt on a second side of the separation zone. The second hold down belt may be offset in a cross-machine direction from the cutting device. The method may comprise moving the second hold down belt over a second portion of the third radial outer surface of the anvil roll and using the second hold down belt to hold portions of the continuous web against the second portion of the third radial outer surface. The method may comprise providing a plurality of fluid ports in the third radial outer surface of the anvil roll and applying a fluid pressure to at least some of the plurality of fluid ports only in the separation zone.

The cutting device may extend radially outwardly, relative to the first axis of rotation, from the first radial outer surface of the cutting roll a first distance. The bearer ring on the cutting roll may extend radially outwardly, relative to the first axis of rotation, from the first radial outer surface of the cutting roll a second distance. The first distance may be the same as or different than the second distance.

Another method of separating discrete articles from a continuous web or a continuous web of articles is provided. The method may comprise providing a cutting roll comprising a first axis of rotation, a first radial outer surface, and a cutting device extending radially outwardly, relative to the first axis of rotation, from the first radial outer surface. The method may comprise providing an anvil roll comprising a second axis of rotation, a second radial outer surface, and a plurality of angularly spaced anvil surfaces on, or extending radially outwardly from, the second radial outer surface, relative to the second axis of rotation. The method may comprise providing a fixed first bearer ring surrounding a portion of the anvil roll or a portion of the cutting roll. The first fixed bearer ring may have a third radial outer surface. The method may comprise providing a second bearer ring surrounding a portion of the anvil roll or a portion of the cutting roll. The second bearer ring may have a fourth radial outer surface. The method may comprise providing a bearing member positioned at least partially intermediate the portion of the anvil roll or the portion of the cutting roll and the second bearer ring. The second bearer ring may be configured to rotate about the first axis of rotation, if on the cutting roll, independent of the rotation of the cutting roll, and may be configured to rotate about the second axis of rotation, if on the anvil roll, independent of the rotation of the anvil roll. The method may comprise positioning the anvil roll and the cutting roll such that the first axis of rotation is generally parallel to the second axis of rotation, and such that the third radial outer surface of the first fixed bearer ring is in contact with the fourth radial outer surface of the second bearer ring. The method may comprise rotating the anvil roll about the second axis of rotation, using the first fixed bearer ring to drive the second bearing ring, conveying the continuous web intermediate the anvil roll and the cutting roll, and separating a discrete article from the continuous web by cutting the continuous web intermediate one of the plurality of anvil surfaces and the cutting device in a separation zone.

The first fixed bearer ring may be flush with or recessed relative to the first radial outer surface, if on the cutting roll or the first fixed bearer ring may be flush with or recessed relative to the second radial outer surface, if on the anvil roll.

The second bearer ring may be flush with or recessed relative to the first radial outer surface, if on the cutting roll or the second bearer ring may be flush with or recessed relative to the second radial outer surface, if on the anvil roll.

General Description of an Example Article

Figure 13:
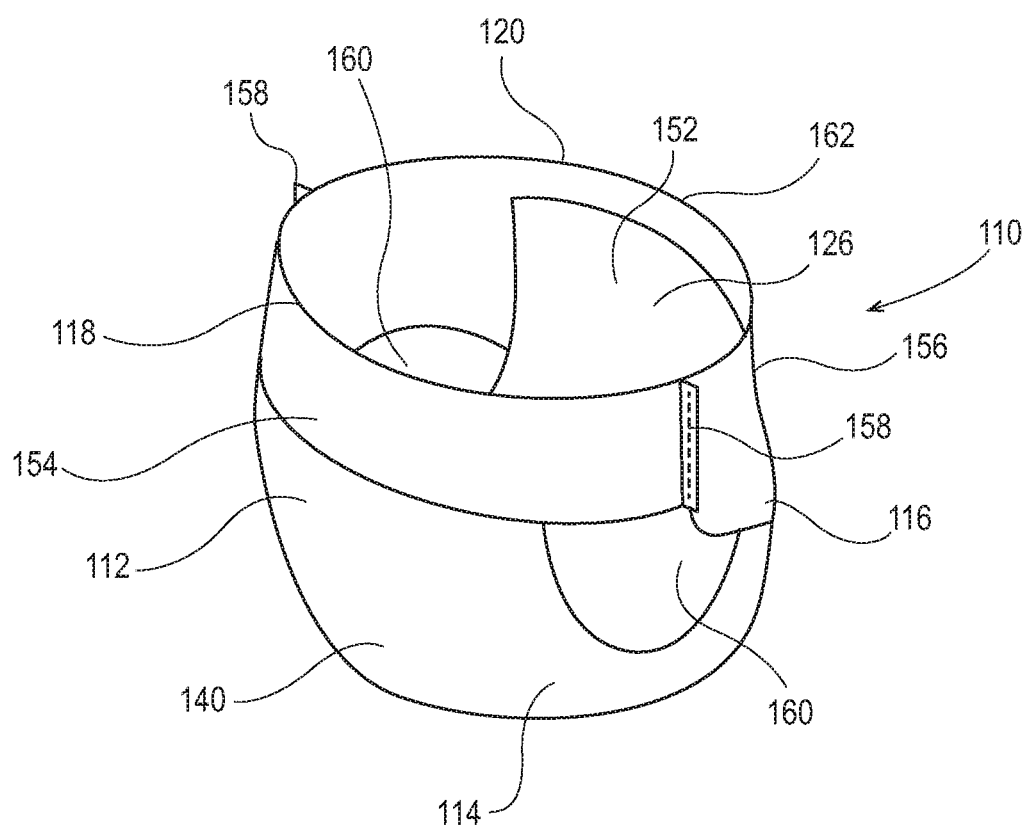
FIG. 13 is a front perspective view of an example absorbent article in the form of a pant that may be separated from a continuous web by the separation assembly.
Figure 14:
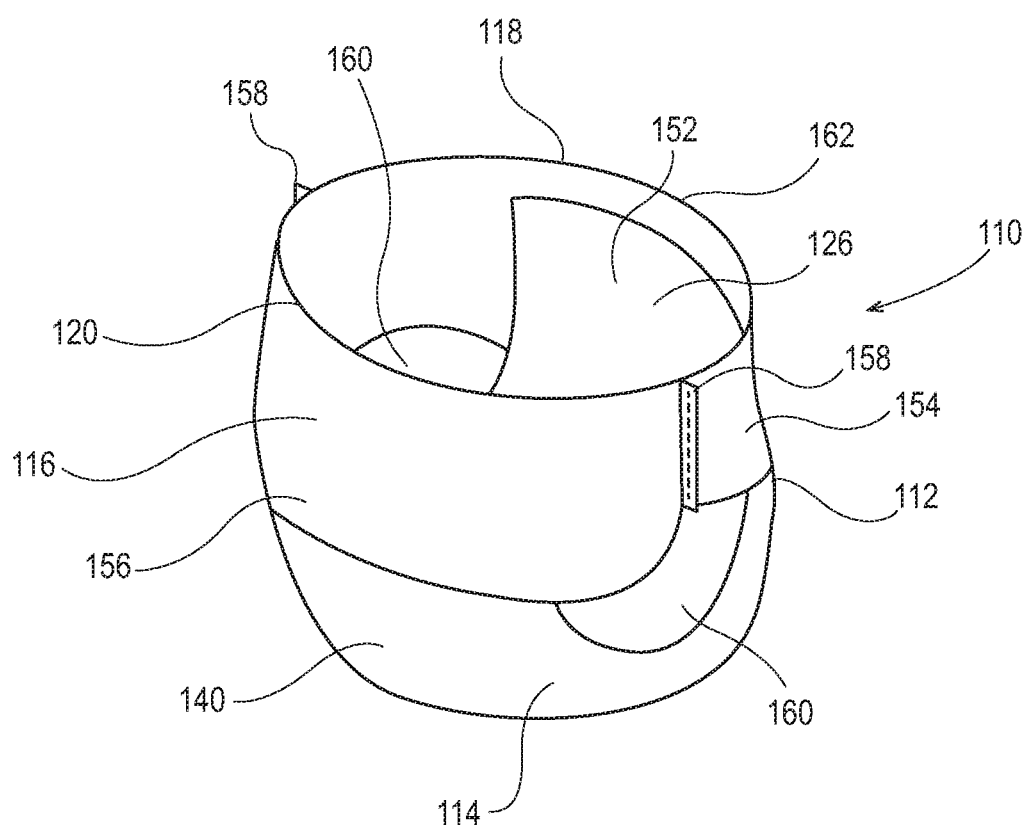
FIG. 14 is a rear perspective view of the example absorbent article of FIG. 13.

An example article that may be separated from the continuous web 12, using the separation assembly, is shown in the form of a pant in FIGS. 13 and 14. FIG. 13 is a front perspective view of a pant 110. FIG. 14 is a rear perspective view of the pant 110. The pant 110 may be a child or toddler training pant or an adult incontinence pant, for example. FIG. 15 is an example plan view of a pant in a flat, laid-out state with elastic contraction removed and with side seams separated. In FIG. 15, a garment-facing surface 202 of the absorbent article 10 is facing the viewer. FIG. 16 is a cross-sectional view of a first belt portion 154 taken about line 16-16 of FIG. 15. FIG. 17 is a cross-sectional view of a second belt portion 156 taken about line 17-17 of FIG. 15. The pant 110 of FIGS. 13-17 is shown for illustration purposes only as the separation assembly may be used to separate any suitable discrete articles from a continuous web.

Referring to FIGS. 13-17, the pant 110 may comprise a front waist region 112, a crotch region 114, and a back waist region 116. The crotch region 114 may extend intermediate the front waist region 112 and the back waist region 116. The pant 110 may comprise a front end edge 118, a back end edge 120 opposite to the front end edge 118, a first side edge 122, and a second side edge 124 opposite to the first side edge 122.

The pant 110 may comprise a liquid permeable topsheet 126, a liquid impermeable backsheet 128, an absorbent core 130 positioned at least partially intermediate the topsheet 126 and the backsheet 128. The pant 110 may also comprise one or more pairs of barrier leg cuffs comprising one or more pairs of leg elastics 134 and one or more acquisition materials 138. The acquisition material or materials 138 may be positioned intermediate the topsheet 26 and the absorbent core 130. As an example, one of the acquisition materials may comprise a nonwoven material and another of the acquisition materials may comprise cross-linked cellulosic fibers. An outer cover material 140 may cover a garment-facing side of the backsheet 128. The pant 110 may have a lateral axis 148 and a longitudinal axis 150.

The pant 110 may have a chassis 152 (sometimes referred to as a central chassis or central panel) comprising the topsheet 126, the backsheet 128, and the absorbent core 130 disposed intermediate the topsheet 126 and the backsheet 128, and one or more of the optional acquisition materials 138. The pant 110 may comprise a front or first belt portion 154 in the front or first waist region 112 and a back or second belt portion 156 in the back or second waist region 116. The chassis 152 may be joined to a wearer-facing surface of the belt portions 154, 156 or to a garment-facing surface of the belt portions 154, 156. Side areas of the front belt portion 154 may be joined to side areas of the back belt portion 156 to form two side seams 158. The sides seams 158 may be any suitable side seams known to those of skill in the art, such as butt seams or overlap seams, for example. When the seams 158 are permanently formed or refastenably closed, the pant 10 has two leg openings 160 and a waist opening circumference 162. The side seams 158 may be permanently joined using adhesives or bonds, for example, or may be refastenably closed using hook and loop fasteners, for example. Referring to FIGS. 15 and 16, the front belt portion 154 may comprise a first nonwoven material 164 and a second nonwoven material 166. A plurality of elastic elements 168 (e.g., elastic stands, elastic strips) may be positioned intermediate the first and second nonwoven materials 164, 166. In some instances, an elastic film may be used instead of, or in addition to, the elastic elements 168. The elastic elements 168 or film may be relaxed (including being cut) to reduce elastic strain over the absorbent core 130 or may alternatively run continuously across the absorbent core 130. Referring to FIGS. 15 and 17, the back belt portion 156 may comprise a first nonwoven material 164 and a second nonwoven material 166. A plurality of elastic elements 168 (e.g., elastic stands, elastic strips) may be positioned intermediate the first and second nonwoven materials 164, 166. In some instances, an elastic film may be used instead of, or in addition to, the elastic elements 168. The elastic elements 168 or film may be relaxed (including being cut) to reduce elastic strain over the absorbent core 130 or may alternatively run continuously across the absorbent core 130. Referring to FIGS. 15-17, the elastics elements 168 may have uniform or variable elastic element spacing therebetween in either of the belt portions. The elastic elements may also be pre-strained the same amount or different amounts. The first and/or second belt portions 154 and 156 may have one or more elastic element free zones 170 where the chassis 152 overlaps the belt portions 154, 156. In other instances, at least some of the elastic elements 168 may extend across the chassis 152.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of separating discrete articles from a continuous web, the method comprising:
    providing a cutting roll comprising:
        a first axis of rotation;
        a first radial outer surface; and
        a cutting device extending radially outwardly, relative to the first axis of rotation, from the first radial outer surface;
    providing a bearer ring on the cutting roll that extends more radially outwardly than the first radial outer surface of the cutting roll relative to the first axis of rotation, wherein the bearer ring comprises a second radial outer surface;
    providing a bearing member positioned at least partially intermediate a portion of the cutting roll and the bearer ring, wherein the bearer ring is configured to rotate about the first axis of rotation independent of the cutting roll;
    providing an anvil roll comprising:
        a second axis of rotation;
        a third radial outer surface; and
        a plurality of angularly spaced anvil surfaces on, or extending radially outwardly from, the third radial outer surface;
    positioning the anvil roll and the cutting roll such that the first axis of rotation is generally parallel to the second axis of rotation, and such that the second radial outer surface of the bearer ring is in contact with a portion of the anvil roll;
    rotating the anvil roll about the second axis of rotation;
    using the anvil roll to drive the bearer ring about the first axis of rotation at a first speed;
    rotating the cutting roll at a second, different speed about the first axis of rotation independent of the anvil roll and the bearer ring;
    conveying the web intermediate the anvil roll and the cutting roll; and
    separating a discrete article from the continuous web by cutting the continuous web intermediate one of the plurality of anvil surfaces and the cutting device in a separation zone.

2. The method of claim 1, wherein the plurality of anvil surfaces are formed on an anvil surface surrounding a portion of the anvil roll or surrounding a portion of the third radial outer surface.

3. The method of claim 1, wherein the plurality of anvil surfaces comprise a plurality of angularly spaced anvil members, wherein the anvil members extend radially outwardly, relative to the second axis of rotation, from the third radial outer surface of the anvil roll.

4. The method of claim 1, wherein the bearing member comprises a plurality of bearings.

5. The method of claim 1, wherein the bearing member comprises a bearing surface.

6. The method of claim 1, wherein the bearing ring surrounds a portion of the first radial outer surface of the cutting roll.

7. The method of claim 1, comprising:
    providing a second bearer ring surrounding a portion of the anvil roll, wherein the second bearer ring has a fourth radial outer surface, and wherein the fourth radial outer surface of the second bearer ring is in contact with the second radial outer surface of the bearer ring on the cutting roll.

8. The method of claim 1, comprising:
    providing at least a second cutting roll comprising:
        a third axis of rotation;
        a fourth radial outer surface; and
        a second cutting device extending radially outwardly, relative to the third axis of rotation, from the fourth radial outer surface;

providing a second bearer ring on the second cutting roll, wherein the second bearer ring extends more radially outwardly than the fourth radial outer surface of the cutting roll, and wherein the second bearer ring comprising a fifth radial outer surface;

providing a second bearing member positioned at least partially intermediate a portion of the cutting roll and the second bearer ring, wherein the second bearer ring is configured to rotate about the third axis of rotation independent of second cutting roll;

moving the cutting roll a distance from the anvil roll such that the cutting roll is not in contact with the anvil roll;

positioning the anvil roll and the second cutting roll such that the second axis of rotation of the anvil roll is generally parallel to the third axis of rotation of the second cutting roll, and such that the fifth radial outer surface of the second bearer ring is in contact with a portion of the anvil roll;

rotating the anvil roll about the second axis of rotation;

using the anvil roll to drive the second bearer ring about the third axis of rotation at a third speed;

rotating the second cutting roll at a fourth speed about the third axis of rotation independent of the anvil roll and the second bearer ring;

conveying a second continuous web intermediate the anvil roll and the second cutting roll; and separating a second discrete article from the second continuous web by cutting the second continuous web intermediate one of the plurality of anvil surfaces and the second cutting device.

9. The method of claim 8, comprising:
providing a third bearer ring surrounding a portion of the anvil roll, wherein the third bearer ring has a sixth radial outer surface, and wherein the sixth radial outer surface of the second bearer ring is in contact with the fifth radial outer surface of the bearer ring on the second cutting roll.

10. The method of claim 9, wherein the second discrete article has a different pitch than the discrete article.

11. The method of claim 10, wherein the cutting roll has a different diameter than the second cutting roll.

12. The method of claim 11, comprising:
rotating the cutting roll about the first axis of rotation independent of the anvil roll and the bearer ring at a first, constant angular velocity before the moving step; and
rotating the second cutting roll about the third axis of rotation independent of the anvil roll and the second bearer ring at a second, different, constant angular velocity after the moving step.

13. The method of claim 8, wherein the cutting roll has the same diameter as the second cutting roll.

14. The method of claim 1, comprising:
providing a first hold down belt on a first side of the separation zone, wherein the first hold down belt is offset in a cross-machine direction from the cutting device;
moving the first hold down belt over a first portion of the third radial outer surface of the anvil roll; and
using the first hold down belt to hold portions of the continuous web against the first portion of the third radial outer surface.

15. The method of claim 14, comprising:
providing a second hold down belt on a second side of the separation zone, wherein the second hold down belt is offset in a cross-machine direction from the cutting device;
moving the second hold down belt over a second portion of the third radial outer surface of the anvil roll; and
using the second hold down belt to hold portions of the continuous web against the second portion of the third radial outer surface.

16. The method of claim 15, comprising:
providing a plurality of fluid ports in the third radial outer surface of the anvil roll; and
applying a fluid pressure to at least some of the plurality of fluid ports only in the separation zone.

17. The method of claim 1, wherein the cutting device extends radially outwardly, relative to the first axis of rotation, from the first radial outer surface of the cutting roll a first distance, wherein the bearer ring extends radially outwardly, relative to the first axis of rotation, from the first radial outer surface of the cutting roll a second distance, and wherein the first distance is different than the second distance.

18. A method of separating discrete articles from a continuous web, the method comprising:
providing a cutting roll comprising:
a first axis of rotation;
a first radial outer surface; and
a cutting device extending radially outwardly, relative to the first axis of rotation, from the first radial outer surface;
providing an anvil roll comprising:
a second axis of rotation;
a second radial outer surface; and
a plurality of angularly spaced anvil surfaces on, or extending radially outwardly from, the second radial outer surface, relative to the second axis of rotation;
providing a fixed first bearer ring surrounding a portion of the anvil roll or a portion of the cutting roll, wherein the first fixed bearer ring has a third radial outer surface;
providing a second bearer ring surrounding a portion of the anvil roll or a portion of the cutting roll, wherein the second bearer ring has a fourth radial outer surface;
providing a bearing member positioned at least partially intermediate the portion of the anvil roll or the portion of the cutting roll and the second bearer ring, wherein the second bearer ring is configured to rotate about the first axis of rotation, if on the cutting roll, independent of the rotation of the cutting roll, and is configured to rotate about the second axis of rotation, if on the anvil roll, independent of the rotation of the anvil roll;
positioning the anvil roll and the cutting roll such that the first axis of rotation is generally parallel to the second axis of rotation, and such that the third radial outer surface of the first fixed bearer ring is in contact with the fourth radial outer surface of the second bearer ring;
rotating the anvil roll about the second axis of rotation;
using the first fixed bearer ring to drive the second bearing ring;
conveying the continuous web intermediate the anvil roll and the cutting roll; and
separating a discrete article from the continuous web by cutting the continuous web intermediate one of the plurality of anvil surfaces and the cutting device in a separation zone.

19. The method of claim 18, wherein the first fixed bearer ring is flush with or recessed relative to the first radial outer surface, if on the cutting roll, or wherein the first fixed bearer ring is flush with or recessed relative to the second radial outer surface, if on the anvil roll.

20. The method of claim 18, wherein the second bearer ring is flush with or recessed relative to the first radial outer surface, if on the cutting roll, or wherein the second bearer ring is flush with or recessed relative to the second radial outer surface, if on the anvil roll.

* * * * *